United States Patent
Boone, III et al.

(10) Patent No.: US 8,945,104 B2
(45) Date of Patent: *Feb. 3, 2015

(54) MICRODERMABRASION SYSTEM WITH COMBINATION SKIN THERAPIES

(75) Inventors: N. Brendon Boone, III, Encino, CA (US); Basil M. Hantash, East Palo Alto, CA (US); Kenneth B. Karasiuk, Oak Park, CA (US)

(73) Assignee: Envy Medical, Inc., Westlake Village, CA (US)

(*) Notice: Subject to any disclaimer, the term of this patent is extended or adjusted under 35 U.S.C. 154(b) by 1318 days.

This patent is subject to a terminal disclaimer.

(21) Appl. No.: 12/197,065

(22) Filed: Aug. 22, 2008

(65) Prior Publication Data

US 2010/0049177 A1 Feb. 25, 2010

(51) Int. Cl.
| | | |
|---|---|---|
| *A61B 18/18* | (2006.01) | |
| *A61B 17/50* | (2006.01) | |
| *A61N 5/06* | (2006.01) | |
| *A61H 9/00* | (2006.01) | |
| *A61B 18/20* | (2006.01) | |
| *A61B 17/00* | (2006.01) | |
| *A61B 17/30* | (2006.01) | |
| *A61B 17/32* | (2006.01) | |
| *A61B 18/00* | (2006.01) | |
| *A61H 23/02* | (2006.01) | |
| *A61N 1/32* | (2006.01) | |

(Continued)

(52) U.S. Cl.
CPC ............ *A61N 5/0616* (2013.01); *A61H 9/0057* (2013.01); *A61B 18/18* (2013.01); *A61B 18/203* (2013.01); *A61B 2017/00734* (2013.01); *A61B 2017/00747* (2013.01); *A61B 2017/306* (2013.01); *A61B 2017/320004* (2013.01); *A61B 2017/320012* (2013.01); *A61B 2018/00023* (2013.01); *A61B 2018/00452* (2013.01); *A61B 2018/0047* (2013.01); *A61B 2218/008* (2013.01); *A61H 23/0263* (2013.01); *A61N 1/328* (2013.01); *A61N 5/062* (2013.01); *A61N 7/00* (2013.01); *A61N 2005/0644* (2013.01); *A61N 2005/0652* (2013.01); *A61B 18/14* (2013.01); *A61B 2018/00994* (2013.01)
USPC .............................................. 606/9; 606/131

(58) Field of Classification Search
CPC ................ A61B 17/54; A61B 17/545; A61B 2017/00747; A61B 2017/00761; A61B 2017/320004; A61B 2018/00452; A61B 2018/00994; A61N 5/0616; A61N 2005/0644
USPC ....................................................... 606/9, 131
See application file for complete search history.

(56) References Cited

U.S. PATENT DOCUMENTS 3,559,542 A * 2/1971 Clapp .......................... 396/530
5,395,361 A * 3/1995 Fox et al. ........................ 606/15

(Continued)

FOREIGN PATENT DOCUMENTS

| KR | 10-2004-0093706 A | 11/2004 |
| KR | 10-2006-0031262 A | 4/2006 |
| WO | 2008052198 A2 | 5/2008 |

*Primary Examiner* — Lynsey Crandall
*Assistant Examiner* — Nathan J Jenness
(74) *Attorney, Agent, or Firm* — Aka Chan LLP

(57) ABSTRACT

A microdermabrasion system offers a combination of other skin therapies in conjunction with microdermabrasion. In an implementation, the system applies light therapy, photodynamic therapy, radio frequency and microwave energy therapy, massage therapy, or combinations of these while exfoliating the skin.

30 Claims, 13 Drawing Sheets

(51) Int. Cl.
*A61N 7/00* (2006.01)
*A61B 18/14* (2006.01)

(56) References Cited

U.S. PATENT DOCUMENTS

| | | | |
|---|---|---|---|
| 6,508,813 B1 * | 1/2003 | Altshuler | 606/9 |
| 6,695,853 B2 * | 2/2004 | Karasiuk | 606/131 |
| 6,926,681 B1 * | 8/2005 | Ramey et al. | 601/6 |
| 7,658,742 B2 * | 2/2010 | Karasiuk | 606/131 |
| 8,236,008 B2 * | 8/2012 | Boone et al. | 606/131 |
| 2002/0016601 A1 * | 2/2002 | Shadduck | 606/131 |
| 2002/0133149 A1 | 9/2002 | Bessette | |
| 2003/0181938 A1 * | 9/2003 | Roth et al. | 606/191 |
| 2003/0212415 A1 * | 11/2003 | Karasiuk | 606/131 |
| 2004/0147984 A1 * | 7/2004 | Altshuler et al. | 607/88 |
| 2005/0037034 A1 * | 2/2005 | Rhoades | 424/401 |
| 2007/0156124 A1 * | 7/2007 | Ignon et al. | 606/9 |
| 2008/0103563 A1 * | 5/2008 | Powell et al. | 607/89 |
| 2009/0222023 A1 * | 9/2009 | Boone et al. | 606/131 |

* cited by examiner

MICRODERMABRASION SYSTEM WITH COMBINATION SKIN THERAPIES

BACKGROUND OF THE INVENTION

The invention relates to the field of devices to treat human skin and more specifically to a device capable of delivering a combination of skin therapies.

As people age, they look for ways to maintain a youthful appearance. Some invasive cosmetic techniques include surgical approaches including eye lifts, face lifts, skin grafts, and breast lifts. However, these invasive techniques also have risks and potential complications. Some people have died during cosmetic surgery operations. Therefore, it is desirable to have noninvasive cosmetic techniques.

There are many different kinds of noninvasive or minimally invasive cosmetic techniques. One technique is microdermabrasion. Microdermabrasion is a process for removing dead cells from the outermost layer of the skin (the epidermis) to provide a younger and healthier looking appearance, remove wrinkles, clean out blocked pores, remove some types of undesirable skin conditions that can develop, and enhance skin tone.

Another technique is light therapy or photomodulation of the tissue. Light therapy involves transmitting light into the skin. Different color lights may be used to treat different types of skin conditions. For example, blue or violet light has been shown in some studies to reduce acne by killing certain bacteria in the pores. Photodynamic therapy (PDT) is another related technique. PDT involves applying a fluid containing a photosensitizing agent to a patient's skin. The photosensitizing agent is activated with a specific wavelength of light, such as ultraviolet light. The technique provides, for example, a reduction of blotchy pigmentation, rough spots (actinic keratosis), and brown spots (lentigos).

Radio frequency (RF) or microwave energy applied to the skin is yet another technique. This involves thermally heating the collagen bundles in the skin. The heat causes the collagen to shrink or contract which removes wrinkles.

Finally, massage therapy can stimulate the flow of blood and oxygen to improve the elasticity of the skin.

People, however, often have very busy lives. They may not have the time to make different appointments for microdermabrasion, light therapy, photodynamic therapy, RF or microwave energy therapy, or massages. Moreover, even if they do have the time for all these appointments, they will not realize the synergistic benefits that may result when different therapies are administered simultaneously.

Therefore, there is a need to provide improved skin therapies.

BRIEF SUMMARY OF THE INVENTION

The present invention relates to skin therapy devices. An embodiment of the current invention is the combination of microdermabrasion, light therapy, photodynamic therapy, radio frequency (RF) and microwave energy therapy, and massage therapy into a single device having various combinations of these therapies (e.g., microdermabrasion with light therapy and RF energy therapy, microdermabrasion with massage therapy, microdermabrasion with light therapy, and microdermabrasion with RF energy therapy).

In an embodiment, a microdermabrasion system includes a console, a hand piece including a tip, connected to a fluid tube connected to the console, where the tip includes an abrading surface formed on a front surface of the tip and a plurality of fluid channels, where the plurality of fluid channels terminate on a side surface of the tip, a vacuum opening, connected to a vacuum tube connected to the console, where the vacuum opening is outside a periphery of the tip, and a plurality of radiation sources, each radiation source connected to an electrical wire connected to the console.

The plurality of radiation sources may be between the tip and the vacuum opening. The plurality of radiation sources may be evenly distributed about a perimeter of the front surface of the tip. An angle between the radiation sources may be 360 degrees divided by a total number of radiation sources. The plurality of radiation sources may be positioned above the tip or on a same plane as the tip.

In an embodiment, the plurality of radiation sources includes at least one of a light emitting diode, a laser diode, a radio frequency diode, or a microwave antenna.

At least one radiation source in the plurality of radiation sources may emit a light beam having a wavelength that is in the visible range. The light beam may be blue, red, or yellow.

In an embodiment there is a radiation source holder, where the plurality of radiation sources are mounted to the radiation source holder and the radiation source holder is made of a thermally conductive plastic.

The plurality of radiation sources may irradiate a region of tissue between the perimeter of the front surface of the tip and the vacuum opening.

The hand piece may further include a vibrating component, a battery, and a switch, connected between the vibrating component and the battery. The vibrating component may include a motor, a weight, and a shaft, connected between the motor and the weight.

In an embodiment, a microdermabrasion system includes a console, a hand piece including a tip, connected to a fluid tube connected to the console, where the tip comprises a plurality of bristles connected to a front surface of the tip and a fluid opening, surrounded by the bristles, on the front surface, a vacuum opening, connected to a vacuum tube connected to the console, where the vacuum opening is outside a periphery of the tip, and a plurality of radiation sources, each radiation source connected to an electrical wire connected to the console.

The plurality of bristles may include optical fiber and the plurality of bristles may be connected to the plurality of radiation sources.

In an embodiment, a microdermabrasion device includes a body having a longitudinal axis, a substantially non-abrasive tip attached to an end of said body and having at least one opening therethrough, an abrasive member located internally of said body and tip, a vacuum access opening adapted to apply negative pressure to a skin surface of a patient through said tip outside a periphery of said abrasive member, thereby drawing a portion of the skin into contact with said abrasive member, and a plurality of radiation sources, each radiation source connected to an electrical wire, where the electrical wire passes through a channel in the body.

In an embodiment, a microdermabrasion device includes a tip including an abrading surface formed on a first side, a collar portion on a second side of the tip, a plurality of fluid channels formed on a second side of the tip, each channel extending through the collar through a first edge to a second edge of the tip, where the second edge of the tip is perpendicular to and touches the first side, and an angle between the first side and the first edge is less than ninety degrees, at least one key notch, formed on the collar portion between two channel openings, where a surface of the collar is perpendicular to the first side, and a plurality of radiation sources on a same plane as the abrasive member.

In an embodiment a microdermabrasion device includes a tip including a plurality of bristles connected to a front surface on a first side, a fluid opening, surrounded by the bristles, on the first side, where the fluid opening extends to a second side, opposite to the first side, a first cylindrical side surface, connected to and perpendicular to the first side, a plurality of prongs which extend away from the first cylindrical side surface and toward the second side, and a plurality of radiation sources at least partially surrounding the plurality of bristles.

In an embodiment, a skin treatment system includes an elongated handle including a tubular passageway, an annular vacuum formed around at least a portion of the tubular passageway, a substantially planar abrasive surface, a treatment tip with at least one opening therethrough, where a vacuum is applied outside a periphery of the abrasive surface through the at least one opening, a vacuum source and fluid reservoir, where a flow path is from a distal end of the tubular passageway, outward at the distal end, and into the annular vacuum and when a vacuum is applied, a fluid in the fluid reservoir is drawn into the passageway of the system, applied to skin at a treatment site, and drawn into the annular vacuum, and a plurality of radiation sources connected to the elongated handle, where at least one radiation source is positioned to provide a beam of light into skin at the treatment site.

In an embodiment, a microdermabrasion device includes a hand piece including an elongated handle including a first passageway and a second passageway, a treatment tip, coupled to the handle, including at least a first opening coupled to the first passageway, where the treatment tip has a longest distance across the tip, a second opening, coupled to the second passageway, and a plurality of radiation sources, coupled to the handle, and a distance between a radiation source and the treatment tip is less than twice the longest distance.

A cross section the first and second passageways may include concentric circles, an inner circle is for the first passageway, and an outer circle is for the second passageway. At least one of the radiation source may be positioned between the first opening and the second opening.

A cross section of the tip may include at least two concentric spaces, a first space of the concentric spaces coupled to the first opening, and a second space of the concentric spaces coupled to the second opening.

The treatment tip may be translucent and include an abrasive surface recessed in the treatment tip.

In an embodiment, the first passageway provides output fluid and the second passageway provides suction. In another embodiment, the first passageway provides suction and the second passageway provides output fluid.

At least one of the radiation sources may be outside a periphery of an abrasive surface of the tip.

An embodiment includes a lens cover, coupled to a housing of at least one radiation source, covering the at least one radiation source and providing magnification of radiation emitted by the at least one radiation source.

Another embodiment includes a housing for at least one radiation source, the housing comprising a locking mechanism to removably hold a lens cover over the at least one radiation source.

Other objects, features, and advantages of the present invention will become apparent upon consideration of the following detailed description and the accompanying drawings, in which like reference designations represent like features throughout the figures.

DETAILED DESCRIPTION OF THE INVENTION

This patent application incorporates by reference U.S. patent Ser. No. 12/197,047, filed Aug. 22, 2008; U.S. patent application Ser. No. 12/197,075, filed Aug. 22, 2008; U.S. patent application Ser. No. 29/304,428, filed Feb. 29, 2008; U.S. patent application Ser. No. 29/322,102, filed Jul. 29, 2008; U.S. patent application Ser. No. 29/322,106, filed Jul. 29, 2008; U.S. patent application Ser. No. 12/040,867, filed Feb. 29, 2008; U.S. patent application Ser. No. 10/393,682, filed Mar. 19, 2003; and U.S. Pat. No. 6,695,853, filed Nov. 21, 2001, and issued Feb. 24, 2004.

Figure 1:
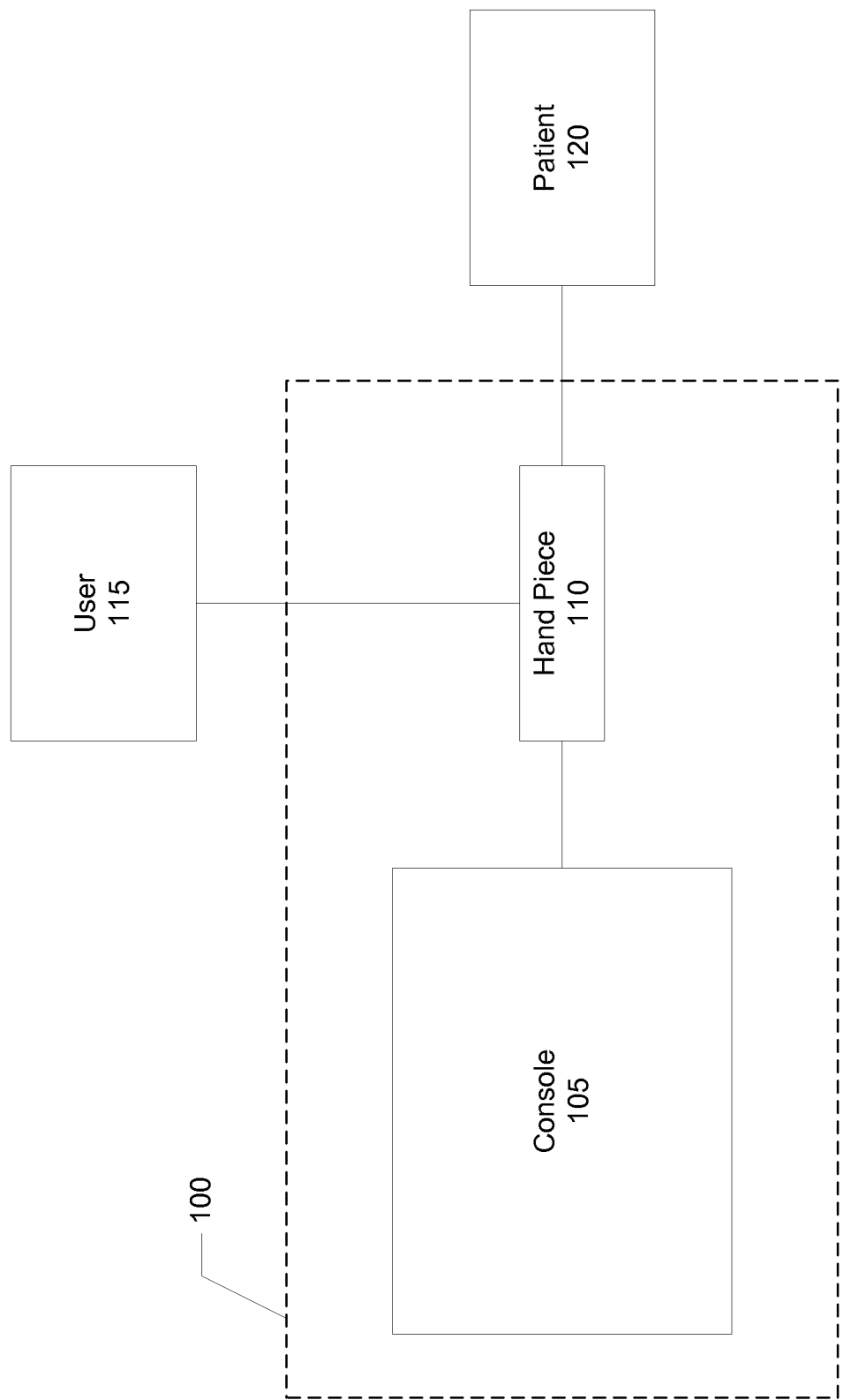
FIG. 1 shows a block diagram of a combination microdermabrasion system according to the present invention.

FIG. 1 is a simplified block diagram of a combination microdermabrasion or dermabrasion system 100. The system has a console 105 which is connected to a hand piece 110. During a microdermabrasion treatment, a user 115 holds the hand piece and runs the hand piece over a patient's 120 skin to exfoliate it.

In various specific embodiments, the hand piece is capable of providing a combination of therapies in conjunction with microdermabrasion exfoliation. These therapies include radiation therapy or massage therapy, or both. Radiation therapy includes light therapy, photodynamic therapy, acoustic therapy, and radio frequency (RF) and microwave energy therapy. The hand piece, in addition to providing the microdermabrasion function, is thus capable of simultaneously emitting radiation (e.g., electromagnetic radiation, visible light, infrared light, near infrared light, ultraviolet light), vibrating, or both.

The user may be a doctor, technician, operator, or aesthetician. After treatment, the patient leaves with a more youthful and healthful appearance.

Figure 2A:
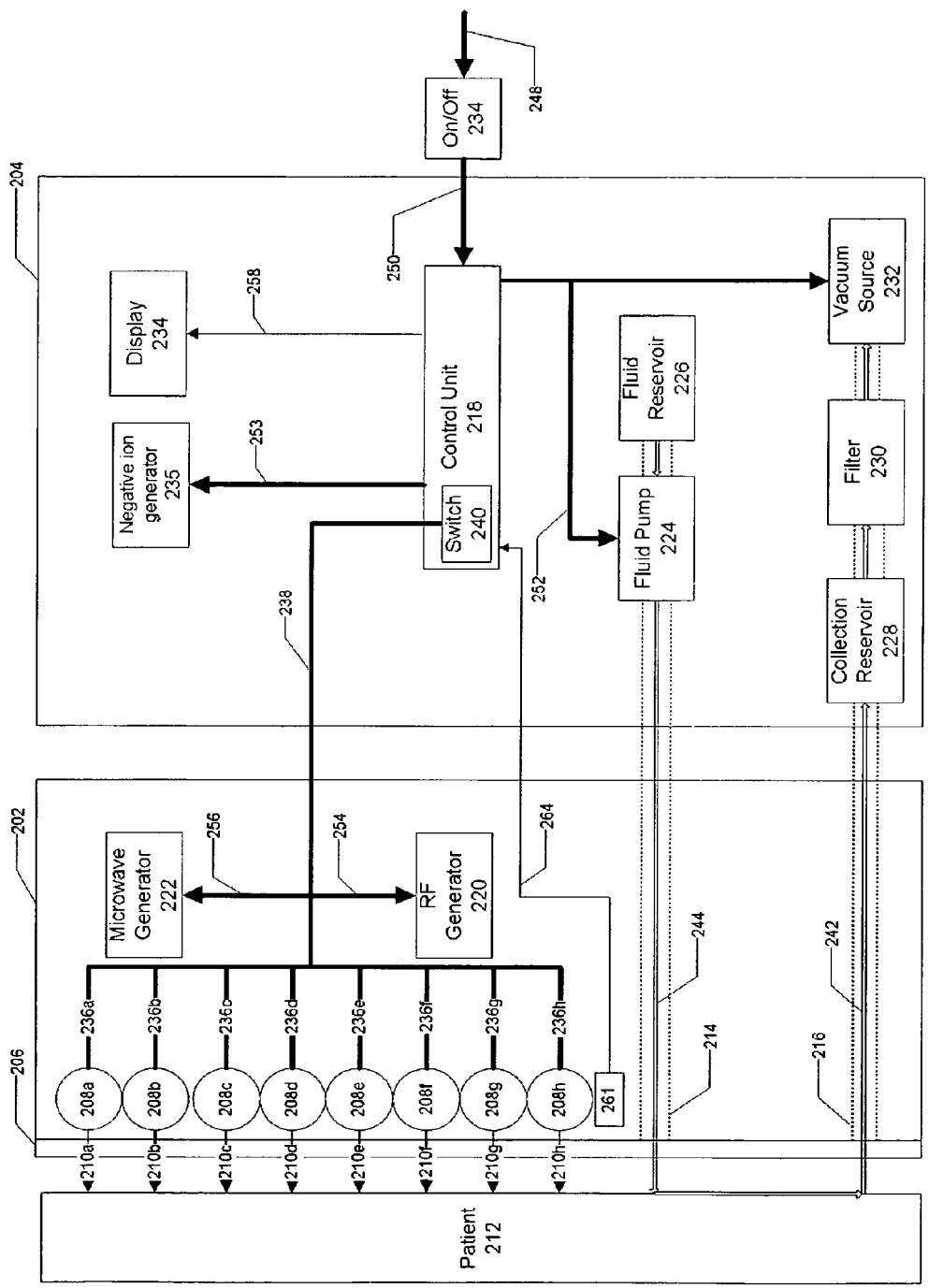
FIG. 2A shows a block diagram of a first embodiment of a combination microdermabrasion hand piece and console according to the present invention.

FIG. 2A shows a block diagram of a hand piece 202 and a console 204. A tip 206 is attached to the hand piece. The hand piece includes one or more radiation sources or emitters 208a, 208b, 208c, 208d, 208e, 208f, 208g, and 208h which emit radiation 210a, 210b, 210c, 210d, 210e, 210f, 210g, and 210h into a patient's 212 skin. The hand piece also includes a fluid delivery line 214 and a vacuum line 216 for microdermabrasion. In a specific embodiment, the hand piece includes a microwave generator 222, a radio frequency (RF) generator, or both. The microwave generator, RF generator, or both may be optional and is not present in some implementations of the invention.

The console includes a control unit 218, a fluid pump 224, a fluid reservoir 226, a collection reservoir 228, a filter 230, a vacuum source 232, and a display 234. In a specific implementation, the console also includes a negative ion generator 235. Via an on-off switch 234, power is supplied to the various components in the console such as the fluid pump, vacuum source, and negative ion generator.

Cables 236a, 236b, 236c, 236d, 236e, 236f, 236g, and 236h connect each radiation source 208a, 208b, 208c, 208d, 208e, 208f, 208g, and 208h, respectively, to a cable 238 which is then connected to a switch 240 in the control unit.

The system has a vacuum path 242 that passes through the vacuum line. The vacuum path includes the vacuum source, which is connected to the filter, which is connected to the collection reservoir. The filter may be optional and is not present in some implementations of the invention. The collection reservoir is connected to the hand piece.

The system has a fluid path 244 that passes through the fluid delivery line. The fluid path includes the fluid reservoir, which is connected to the fluid pump, which is connected to the hand piece. The fluid pump may be optional and is not present in some implementations of the invention; in such a case, the fluid is drawn through the fluid path, through the hand piece, to the collection reservoir by the vacuum source. A fluid may include a gas or liquid, or a combination of these.

The system has a power path to distribute power (e.g., AC or DC, or both) to the components of the system. Power is supplied to the system through a power input line 248 to the on-off switch. From the on-off switch, power is supplied via a line 250 to the control unit. From the control unit, power is supplied via a line 252 to the vacuum source and fluid pump. Power is supplied via a line 253 to the negative ion generator. When power is supplied as AC power (e.g., from an AC outlet), and a component such as the control unit uses DC power, the system will include an AC-to-DC converter to convert AC power to DC power.

From the control unit, power is supplied via cable 238 to the electrical components in the hand piece such as the radiation sources, the microwave generator, and the RF generator. A line 254 connects the RF generator to cable 238. A line 256 connects the microwave generator to cable 238. Lines 254 and 256 supply power to the RF generator and microwave generator, respectively.

The radiation sources may emit radiation at various wavelengths. The radiation may be emitted as, for example, acoustic waves, radio frequency (RF) waves, microwaves, infrared, far-infrared, near-infrared, visible light, ultraviolet light, far-ultraviolet light, near-ultraviolet light, and combinations of these.

In a specific implementation, one or more radiation sources emit visible light. Visible light is generally electromagnetic radiation having a range of wavelengths from about 380 nanometers to about 750 nanometers.

In some applications it may be desirable to direct a single band or selected multiple bands of visible light waves into the patient's skin. Thus, in a specific implementation, the radiation sources include light emitting diodes (LEDs) which emit a predominately blue light, red light, yellow light, green light, or combinations of these. The radiation sources may include light having a luminance (candela per square meter) that may be two, three, four, or more than four times greater than the ambient light.

Blue light is typically light having a predominate wavelength of about 470 nanometers, but may range from about 450 nanometers to about 495 nanometers. Red light is typically light having a predominate wavelength of about 640 nanometers, but may range from about 620 nanometers to about 750 nanometers. Yellow light is typically light having a predominate wavelength of about 590 nanometers, but may range from about 570 nanometers to about 590 nanometers. Green light is typically light having a predominate wavelength of about 510 nanometers, but may range from about 510 nanometers to about 570 nanometers.

These particular wavelengths of light may be used to treat a variety of skin conditions by transmitting the light into the patient's skin. For example, blue light may be transmitted into the patient's skin in order to treat acne. Red light may be transmitted into the patient's skin to reduce pigmentation and lighten the skin. Yellow light may be transmitted into the patient's skin to promote the production of collagen which reduces fine lines and wrinkles.

In a specific embodiment using LEDs as radiation sources, all of the LEDs emit the same color light. Such an embodiment may be used to provide a focused treatment of a specific skin condition. For example, a teenager with acne problems may undergo treatment with only blue light. These patients, because of their young age, may not yet have the fine lines and wrinkles associated with older patients.

In another embodiment, two or more LEDs may simultaneously emit light of different colors which, when combined, create another color of light. For example, a first LED may emit green light. A second LED may emit red light. An implementation of the invention may then include a light mixer to combine the green and red light beams to produce yellow light. It should be appreciated that the light mixer may be used to combine the primary light colors of red, green, and blue in specific ratios to produce a light beam of any color.

In yet another embodiment using LEDs, two or more LEDs may emit light of different colors to treat a combination of skin problems. For example, radiation sources 208a, 208b, and 208c may emit blue light. Radiation sources 208d, 208e, and 208f may emit red light. Radiation sources 208g and 208h may emit yellow light. Such an embodiment may be appropriate for an older adult who suffers from adult acne in addition to pigmentation, fine lines, and wrinkles.

Emitting or transmitting light at different wavelengths (i.e., different colors) also allows, directing treatment to a specific layer of skin (e.g., epithelium, basement membrane, dermis, and subcutis). For example, light at longer wavelengths, such as red light penetrate deeper into the skin than light having shorter wavelengths such as blue light.

However, LEDs are just one example of a radiation source that may be used in an implementation of the invention. In other embodiments of the invention, other types of light sources may be used instead, or additionally. Some examples of a radiation source include a light emitting polymer (LEP), organic light emitting diode (OLED), organic electro-luminescence (OEL) device, superluminescent diode (SLD), edge emitting LED (EELED), surface emitting LED (SELED), laser, laser diode, waveguide laser diode, vertical-cavity surface-emitting laser (VCSEL), fiber laser, fluorescent solid state source, lamp, fluorescent lamp, dichroic lamp, incandescent light bulb, halogen light bulb, xenon light bulb, high intensity discharge lamp, and the like.

It should be appreciated that directing a single color light or selected multiple colors of light into the patient's skin may be accomplished in a variety of ways. One embodiment of the invention includes single color LEDs (e.g., blue, red, green, and yellow LEDs). Another embodiment of the invention includes LEDs capable of producing multiple colors. In yet another embodiment, a broad band radiation source is included with an optical element to filter out unwanted wavelengths.

For example, an embodiment of the invention may include one or more light filters through which the light is transmitted before the light is transmitted into the patient's tissue. For example, the tip may include a light filter that is placed over a radiation source. The light filter may be designed with a shape (e.g., annular shape) so that it can be fit over the radiation sources while still allowing the tip, and fluid and vacuum passageways to be exposed. A release mechanism (e.g., release tab) may be included with the radiation source structure holder so that the user can easily remove and replace the light filter.

Such light filters may be used to absorb some wavelengths of light while allowing other wavelengths of light to pass through and into the patient's tissue. For example, a radiation source may be a light bulb that emits white light. White light is composed of all three primary colors (i.e., red, green, and blue). A colored filter may then be used to produce different colors of light.

For example, white light may be transmitted through a red filter to produce red light. That is, a red filter absorbs blue and green light and lets red light pass. White light may be transmitted through a blue filter to produce blue light. That is, a blue filter absorbs red and green light and lets blue light pass. White light may be transmitted through a yellow filter to produce yellow light. That is, a yellow filter absorbs blue light and permits green and red light to pass. The combination of green and red light produces yellow light.

Some examples of filters that may be used in an implementation of the invention include absorptive, dichroic, monochromatic, infrared, ultraviolet, longpass, shortpass, bandpass, and polarization filters.

Figure 2B:
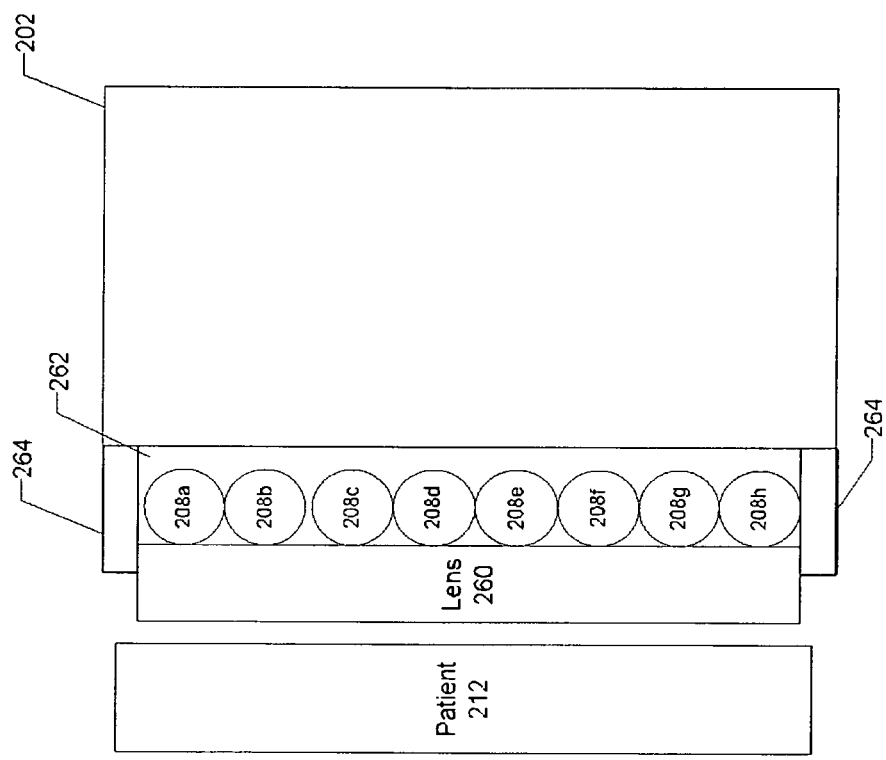
FIG. 2B shows a block diagram of a specific embodiment of a microdermabrasion hand piece with a lens placed over radiation sources.

In other embodiments, as shown in FIG. 2B, a lens 260 may be placed over one or more radiation sources to magnify or focus the radiation emitted by one or more radiation sources. A lens may also be used to protect the radiation sources from damage (e.g., fluid damage). The lens may be designed with a shape (e.g., annular shape) so that it can be fit over the radiation sources while still allowing the tip, and fluid and vacuum passageways to be exposed. A release mechanism 264 (e.g., release tab) may be included with the radiation source structure holder 262 so that the user can easily remove and replace the lens. In some cases it may be desirable to use the lens to magnify the radiation emitted by the radiation sources to provide an effective treatment. However, in other cases, it may instead be desirable to lessen the radiation as may be the case where the patient has sensitive skin. Thus, an embodiment may also include a lens which diverges or attenuates the radiation emitted by one or more radiation sources.

In a specific implementation, one or more optical wave guides, such as optical fiber may be used to transmit light into the patient's tissue. For example, the radiation sources (e.g., LEDs, light bulbs, laser diodes, and the like) may be located in the console as opposed to the hand piece as shown in FIG. 2A. Optical fiber may then be used to transmit light from the console to the hand piece. That is, the tip of the hand piece may include one or more ends of optical fiber. The opposite of ends of the optical fiber may then be coupled to the light sources in the console.

In yet another implementation, the radiation sources may be at a different location in the hand piece instead of at the tip as shown in FIG. 2A. For example, the radiation sources may be located in the hand piece at the opposite end of the tip.

A benefit of using fiber optics is that the cables do not have to include electrical wiring. That is the cables may be passive as opposed to active. This may then, for example, lessen the chances of a shock hazard to the patient and user.

However, locating the radiation sources at the tip may be beneficial in certain applications. For example, there may be less attenuation of the emitted light as the light does not have to travel from the console to the tip.

In yet another implementation, there may be a combination of LEDs and fiber optic cable ends at the tip. For example, a light therapy treatment may include passing light through a patient's skin at different depths. Thus, light from LEDs in the hand piece may be used to penetrate the patient's skin at a deeper depth than light from fiber optic ends in the hand piece.

In a specific implementation, one or more radiation sources are used to therapeutically heat the patient's tissue. The radiation sources may output radiation that has a power or energy level that may be two, three, four, or more than four times greater than the ambient radiation. The heat may be used to degrade the collagen in the tissue. This causes the tissue to shrink and results in the tightening of the skin and reduction of wrinkles. The radiation sources may deliver RF energy, microwave radiation, or both to the patient's skin.

Thus, in a specific embodiment, the radiation sources may include radio frequency electrodes. The electrodes may be in a monopolar configuration, bipolar configuration, or both. Monopolar configurations typically provide a greater depth of RF energy penetration into the tissue, than bipolar configurations. Monopolar configurations typically penetrate to a depth of about 4 millimeters. Bipolar configurations typically penetrate to a depth of about 0.2 millimeters to about 0.3 millimeters. Some implementations may include only bipolar configurations. Because the bipolar configuration penetrates the tissue to a lesser depth than the monopolar configuration, there is less potential for injury to other structures below the skin such as nerves.

The radiation sources, i.e., electrodes, transmit energy to the tissue via radio frequency waves generated by the RF generator. The control unit allows a user to control the RF parameters, such as power level, cycles, and other parameters, such as selecting pulsed RF waves or continuous RF waves.

The radio frequency waves are typically in the range from about 100 kilohertz to about 450 kilohertz. This includes for example, less than 100 kilohertz, 125, 150, 175, 200, 225, 250, 275, 300, 325, 350, 375, 400, 425, or greater than 450 kilohertz.

The electrodes are typically constructed of materials having a high thermal conductivity such as metals. The metals may include stainless steel, tungsten, brass, beryllium, copper, and the like.

In an embodiment using RF energy, the fluids exiting the tip may serve as a conductive fluid (e.g., saline solution) to conduct RF energy to the skin and ensure electrical contact of the electrode with the skin. The fluids may also act as a heat sink. This helps to ensure uniform treatment and prevent thermal injury to the tissue, such as burns.

The hand piece allows the user to control the placement of fluids because the fluids are delivered directly to the treatment site by the hand piece. The hand piece can then vacuum or suction away the fluids from the treatment site. These two features of the invention help to ensure against heating and burning tissue not intended to be treated, as well as preventing shock hazards to the patient and user.

In a manner similar to RF energy, the radiation sources may transmit microwave energy. In this embodiment, the radiation sources may include one or more microwave antennas. The control unit allows the user to control the microwave parameters, such as power level, cycles, and other parameters, such as selecting pulsed microwaves or continuous microwaves.

The microwave generator may generate a frequency range from about 2 gigahertz to about 20 gigahertz.

In a specific implementation, the radiation sources heat the patient's tissue to about 9 degrees Celsius above the ambient temperature. For example, if the ambient temperature is about 21 degrees Celsius then the radiation sources will heat the patient's tissue to about 30 degrees Celsius. However, in other implementations, the patient's tissue is heated to about 59 degrees Celsius above the ambient temperature. For example, if the ambient temperature is about 21 degrees Celsius then the radiation sources will heat the patient's tissue to about 80 degrees Celsius.

Thus, the patient's tissue (e.g., skin) is typically heated to a temperature range of about 30 degrees Celsius to about 80 degrees Celsius.

A specific implementation of the invention includes a temperature sensor or thermostat 261 to help regulate the patient's skin temperature. The temperature sensor may be placed at the tip so that the temperature sensor will be near or in contact with the patient's tissue during treatment. For example, the temperature sensor may be placed near or in contact with the radiation sources as shown in FIG. 2A.

The temperature sensor is connected via a data line 264 to the control unit. The temperature sensor detects the temperature of radiation sources, tissue, or both and communicates this information back to the control unit via the data line. This allows the system to ensure that the patient's tissue is being properly heated. For example, if the temperature of the tissue falls below a threshold level then the control unit will increase power to the radiation sources (e.g., microwave antennas). If the temperature of the tissue exceeds a threshold level then the control unit will decrease power to the radiation sources. Thus, the temperature sensor may also function as a safety feature. That is, if the temperature exceeds a maximum threshold value, the control unit may decrease or disconnect power to the radiation sources to prevent the patient's tissue from being burned.

Switch 240 is coupled to the control unit. Cable 238 extends from the switch, enters the hand piece and is coupled to one or more radiation sources. The switch is user-operated. The switch allows the user to control the amount of power is supplied to the radiation sources. For example, during a treatment session, the patient may have a particularly sensitive area of skin that they do not want exposed to, for example, RF energy. The switch then allows the user to switch off or decrease the power supply to the radiation sources while power continues to flow to the vacuum source and fluid pump.

In an embodiment, the switch is located at the console as shown in FIG. 2A. In other embodiments, the switch is located on the hand piece. In yet another embodiment, the switch may be located between the hand piece and the console.

Although FIG. 2A only shows one switch, other implementations may have multiple switches coupled between the radiation sources and the control unit. For example, there may be two, three, four, five, six, seven, eight, or more than eight switches. These additional switches allow a user to selectively turn on and off individual radiation sources or groups of radiation sources. For example, the radiation sources may include LEDs having varying wavelengths (e.g., blue, red, yellow). Each wavelength may be intended to treat a specific skin condition. A first, second, and third switch may control power to the blue, red, and yellow LEDs, respectively. When a user treats a teenager who only has acne problems, the user may decide to only enable the first switch (i.e., the blue light to treat the acne).

However, the same hand piece can also be used on an adult with both acne and pigmentation problems. In this case, the user would enable both the first and second switches (i.e., blue and red LEDs) to treat the acne and pigmentation.

In an embodiment, multiple switches are used to control different types of radiation sources. For example, the hand piece may include as radiation sources a combination of LEDs, RF electrodes, and microwave antennas. A first, second, and third switch may control power to the LEDs, RF electrodes, and microwave antennas, respectively. The user, depending on the patient's skin condition, may then only enable the first switch for the LEDs, the second switch for the RF electrodes, the third switch for the microwave antennas, or combinations of these.

Furthermore, additional switches may be used to control other components such as the fluid pump, vacuum source, or both. For example, the vacuum source and fluid pump may be controlled by two separate switches. This allows, for example, a "dry" microdermabrasion treatment without fluids. As another example, the user may decide to turn off both the fluid pump and vacuum source to provide only radiation therapy.

A specific implementation of the invention includes negative ion generator 235. The negative ion generator may further include one or more ion-emitting pins or electrodes for producing negative ions in the air which flows past the electrode. A fan may also be included to direct air past the electrodes.

The negative ion generator may be placed in the console as shown in FIG. 2A or placed in the hand piece. The negative ion generator is optional and may not be included in some implementations of the invention.

The negative ion generator may generate negative ions using, for example, a piezoelectric transformer or a voltage generator. The voltage generator may generate voltages that range from about 1600 volts to about 1700 volts. In other implementations, the voltage generator may generate higher voltages that range from about 6000 volts to about 7000 volts.

The negative ion generator generates negative ions by negatively charging gas molecules, such as oxygen molecules and fine particles in the air. Negative ionization may reduce the concentration of airborne contaminates such as pollen, dust, dust mites, viruses, cigarette smoke, animal dander, odors, and fumes from the breathing zone by binding with these contaminates and causing them to fall to the floor.

Figure 3:
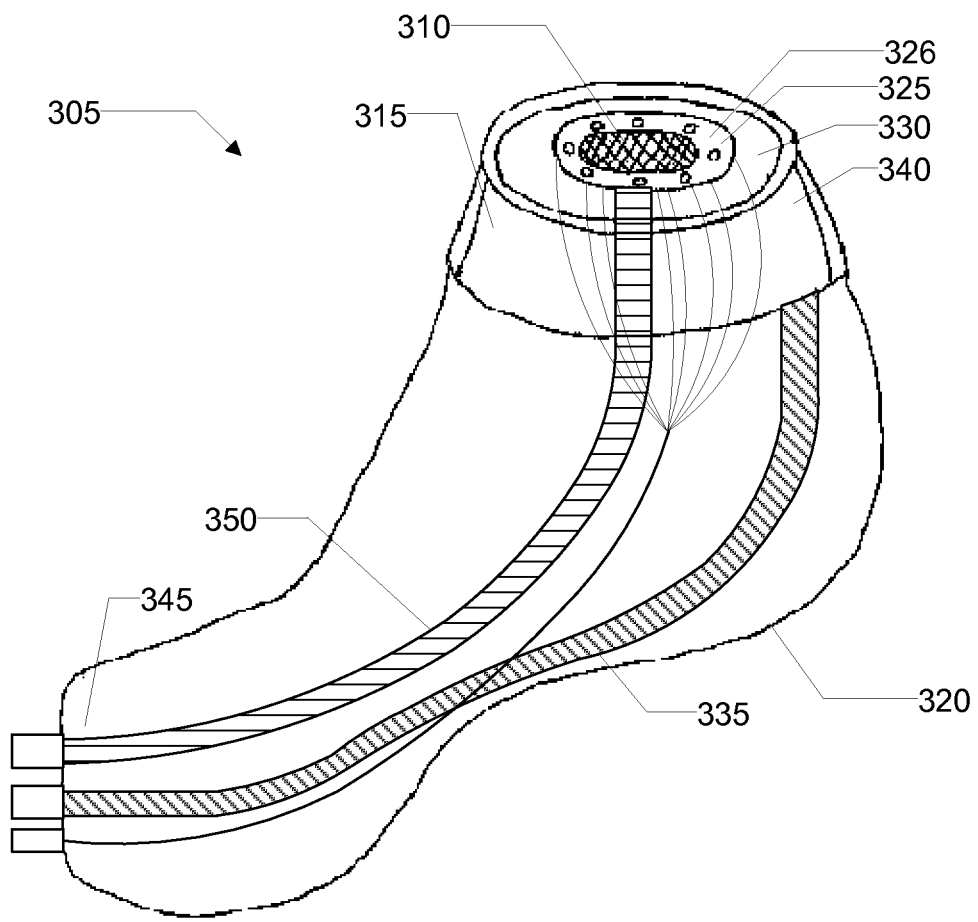
FIG. 3 shows a perspective view of the first embodiment of a combination microdermabrasion hand piece.

FIG. 3 shows a perspective view of a hand piece 305 that provides both microdermabrasion and radiation therapy. A tip 310 (or treatment tip) is placed in a tip holder 315 (or receptacle). The tip holder fits over a handle 320 of the hand piece. The tip holder includes a radiation source holder 325 which surrounds the tip. An annular passageway 330 is formed between the outside perimeter of the radiation source holder and an inside perimeter of the tip holder.

A vacuum line 335 is coupled to the annular passageway. The vacuum line extends from a distal end 340 through the handle and exits at a proximal end 345 where the vacuum line is then connected to a vacuum source. A fluid line 350 is coupled to the tip at the distal end. The fluid line extends from the tip through the handle and exits at the proximal end where the fluid line is then connected to a fluid source. The vacuum and fluid lines are approximately parallel to each other as they travel through the hand piece.

The vacuum and fluid lines are typically made of tubing and are flexible. They may be made of polyvinyl chloride (PVC) or other plastic, for example.

The radiation source holder includes one or more radiation sources as discussed above (e.g., LEDs, RF electrodes, microwave antennas, or combinations of these). The radiation source holder may be at least partially formed of a heat conducting material for dissipating heat generated by the radiation sources. For example, in some applications it may be desirable to dissipate the heat generated by the radiation sources so that the patient's skin is more evenly heated. Thus, the radiation source holder may function as a heat sink and be made of metals such as steel, stainless steel, aluminum, copper, and copper alloys.

The radiation source holder may also be made of ceramic, composite materials (e.g., plastic and carbon fiber), plastic (e.g., nylon), or thermally conductive plastics or polymers. The thermal conductivity of such thermally conductive plastics may range from about 1.0 watts per millikelvin to about 10 watts per millikelvin.

In a specific implementation, a tissue facing surface 326 of the radiation source holder is textured (e.g., knurled) to increase the surface area of the tissue facing surface and thus facilitate heat transfer from the radiation sources to the radiation source holder and to the patient's tissue.

In a specific implementation, the tissue facing surface is also be coated or impregnated with a reflective material to direct radiation emitted by the radiation source into the patient's tissue. Some examples of reflective materials include foils (e.g., aluminum foil and gold foil), mirrors, titanium dioxide, and light-reflective paints.

Figure 4:
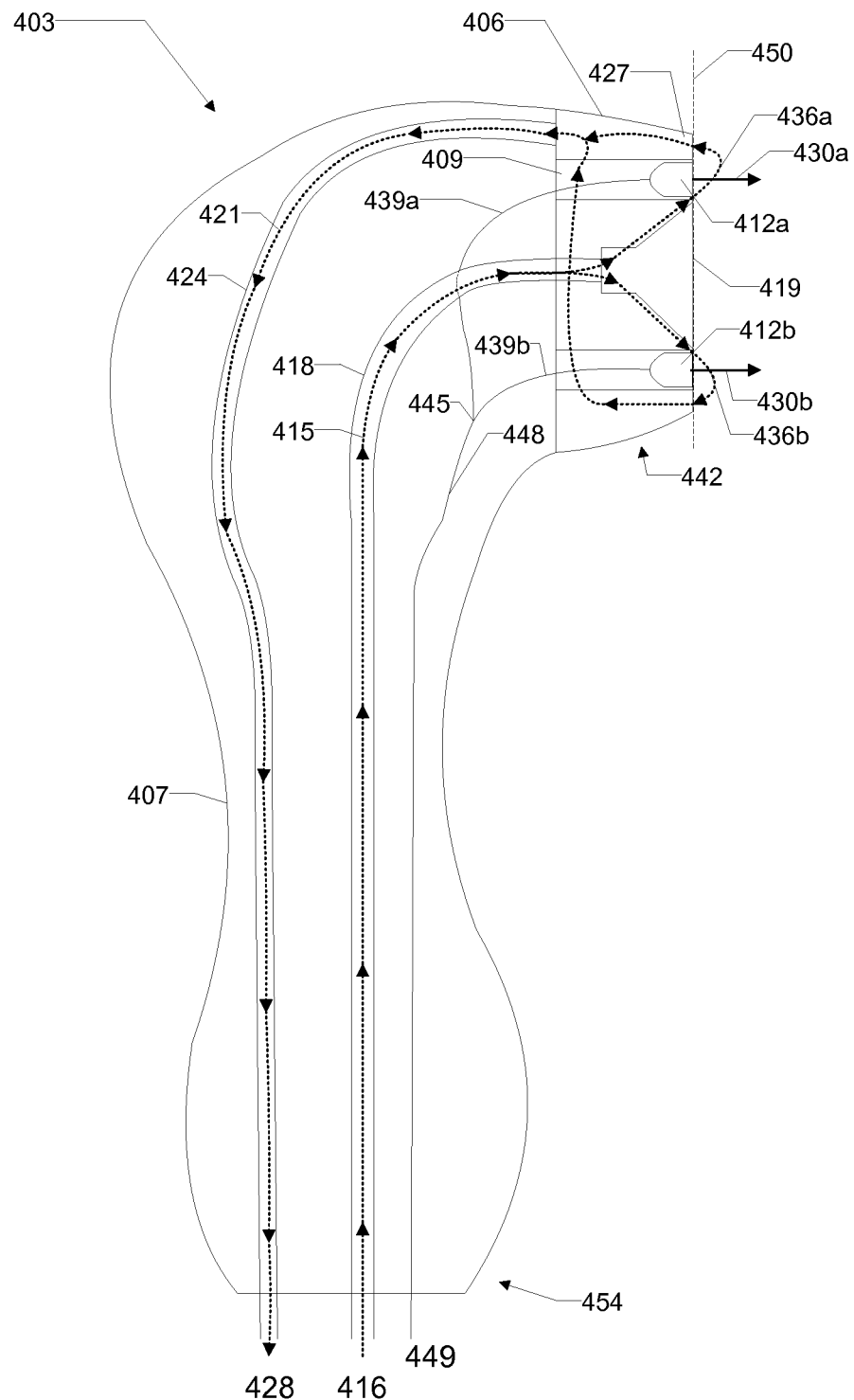
FIG. 4 shows a side view of the first embodiment of a combination microdermabrasion hand piece.

FIG. 4 shows side view of a hand piece 403. The hand piece includes a tip holder 406 and a handle 407. The tip holder includes a radiation source holder 409 which holds one or more radiation sources 412a, and 412b.

A fluid path 415 travels from a fluid source 416 through a fluid delivery line 418 and exits through one or more openings around a tip 419. In a specific implementation, fluid exists through one or more openings in the tip.

A vacuum path 421 in a vacuum line 424 sucks the fluid into an annular passageway 427, which has a negative pressure condition created by a vacuum source 428, and into the vacuum line. The fluid and vacuum paths make up a closed loop vacuum.

One or more beams of radiation 430a and 430b are emitted from one or more radiation sources 412a and 412b which are attached to the radiation source holder. In a specific embodiment, the beams of radiation irradiate a region of tissue between the annular passageway and the tip. In other words, the beams of radiation may irradiate a region of tissue that at least partially surrounds the tissue being abraded. The beams of radiation intercept the fluids in the fluid path at one or more intersections 436a and 436b.

The invention can thus be used for photodynamic therapy (PDT). In PDT, fluids (e.g., aminolevulinic acid) containing photosensitizing agents are applied to the skin. These fluids are sensitive to certain wavelengths of light (e.g., blue light). The intersection of the fluid and radiation paths provide, for example, any light sensitive agents (i.e., photosensitizers) in the fluid to react in a photochemical reaction. PDT can be used to treat, for example, actinic keratoses, acne-related disorders, sun-damaged skin, or aging skin.

Each radiation source is coupled to a cable. For example, a cable 439a is coupled to radiation source 412a and a cable 439b is coupled to radiation source 412b. The cables extend from a distal end 442 of the hand piece and meet at an intersection 445 where they are then enclosed in a single cable 448. Cable 448 continues through the handle and exits at a proximal end 454 of the handle.

In a specific implementation, cable 448, after exiting the handle, may then be connected to a power supply 449. In another configuration, the power supply is contained within the handle.

The cables 439a, 439b, and 448 may include standard electrical wiring (e.g., copper or aluminum wire), which may be stranded, solid core, or both. The cables will typically be enclosed in a cable jacket. The cable jacket is typically constructed of a flexible material. The cable jacket may be made of shrink wrap tubing, plastic, rubber, or vinyl.

The cables may be active and include electrical wiring because the radiation sources may include light emitting diodes (LEDs), electrodes for delivering radio frequency (RF) energy, microwave antennas for delivering microwave energy, or combinations of these.

One or more of the cables may be at least partially enclosed in a channel or conduit within the hand piece. The channel can help to guide and protect the cables so that they do not become tangled with the other components (e.g., fluid and vacuum lines) in the hand piece.

In another implementation, one or more of the cables may be partially or completely outside the hand piece. For example, one or more of the radiation sources may be attached to an external surface of the hand piece. The cable for the radiation source may then be external to the hand piece instead of within the hand piece and may run along the external surface of the hand piece.

In an embodiment, the radiation source holder is integrated with the tip holder as a single piece and is disposable. A plug at intersection 445 may be used to mate cable 448 with the individual cables extending from the radiation sources. For example, the end of cable 448 may include a plug while cables 439a and 439b may converge into a socket which then fits into the plug.

The tip holder may be designed to require less frequent replacement than the tip as the tip holder will not be subject to as much wear and tear as the tip. Different tip holders may also be packaged as a kit for the user. The different tip holders may include different types of radiation sources. For example, a first tip holder may include only blue LEDs, a second tip holder may include both blue and red LEDs, a third tip holder may include only electrodes for RF therapy, a fourth tip holder may include only microwave antennas for microwave energy therapy, a fifth tip holder may include a combination of LEDs, electrodes, and microwave antennas.

Different patients have different types of skin problems. For example, some patients may only have acne problems. Other patients may have both acne and wrinkle problems. The different types of radiation sources allow users to select a specific type of radiation source or a specific combination of radiation sources to customize a patient's treatment and treat specific conditions.

In an embodiment, an integrated connector includes the vacuum or annular passageway, the radiation sources, and fluid openings. The integrated connector may be designed so that the user may detach and reattach the integrated connector. The integrated connector may include a locking mechanism (e.g., insert and twist). Such a design allows the use of different types of integrated connectors with the same hand piece. Thus, different skin therapies may be administered using the same hand piece, but with a different integrated connector.

In yet another embodiment, the radiation source holder may be integrated with the handle as a single piece. The tip holder may remain a separate piece and be designed to be replaced by the user when the tip holder wears out. In this embodiment, it will be less expensive to replace the tip holder because the tip holder will not include the radiation sources and their associated cables.

In yet another embodiment, the radiation source holder, tip holder, and handle are separate pieces. The radiation source holder may be designed such that it can be removed and attached to the handle by a user (e.g., insert radiation source holder into handle and then twist or screw. As another example, the radiation source holder may be designed to snap or press into the handle (i.e., snap fit and press fit).

In an embodiment, the radiation sources are positioned such that they are on a same plane 450 as the tip. That is, the distance from the patient's tissue to the tip and the distance from the patient's tissue to the radiation source will be the same.

However, in other embodiments, one or more radiation sources may not be positioned on the same plane as the tip. That is, the distance from the patient's tissue to the tip and the distance from the patient's tissue to the radiation source will be different. For example, in an embodiment, the radiation sources are positioned such that they are above a plane 450 on the tip. When the tip touches the patient's tissue, the radiation sources are some distance above the area where the tip contacts the tissue.

In another embodiment, the radiation sources are positioned such that they are below an abrasive surface of the tip. For example, the abrasive surface may be recessed in the tip and the tissue is drawn into the recessed portion of the tip. The radiation sources are below this recessed distance. In other embodiments, radiation sources are at the same plane as the recessed abrasive surface. The radiation sources are above the same plane of the recessed abrasive surface. In a further implementation, the tip has a translucent housing (e.g., clear), so the radiation can penetrate through the translucent housing to the tissue surface being drawn into the tip's recessed abrasive surface.

For example, a radiation source may be positioned from about 1 millimeter to about 50 millimeters away from plane 450, including less than 1 millimeter away from plane 450 and more than 50 millimeters away from plane 450. Generally, moving the radiation source away from plane 450 will spread out the radiation (e.g., light beam) coverage on the patient's tissue, but reduce the intensity of the radiation. Conversely, moving the radiation source closer to plane 450 will decrease the radiation coverage on the patient's tissue, but increase the intensity of the radiation. In some applications it may be desirable to increase the radiation coverage and decrease the radiation intensity. In other applications it may be desirable to decrease the radiation coverage and increase the radiation intensity.

In a specific implementation, a cross section of the hand piece, tip, tip holder, radiation source holder, or combinations of these includes at least two concentric spaces, i.e., two spaces having a common center. For example, a cross section taken of fluid delivery line 418 at or near distal end 442 may show a circular shaped fluid path 415, i.e., a first passageway. The cross section may also include annular passageway 427. Thus, the cross section may also show a ring or circular shaped passageway, i.e., a second passageway which surrounds the first passageway. That is, the first passageway includes an inner circle which is surrounded by an outer circle included in the second passageway. The first and second passageways may be concentric, i.e., have a common center.

This concentricity feature of the invention provides certain benefits including, for example, an even distribution of fluids around the target tissue (e.g., surface being abraded) and an even amount of fluid drawn into the annular passageway. That is, one side of the target tissue is not receiving more or less fluid than another side of the target tissue. Similarly, one side of the target tissue is not receiving more or less suction than another side of the target tissue. This provides more uniform results.

In a specific embodiment, the area of the first passageway is the same as the area of the second passageway. In another embodiment, the area of the first passageway is different than the area of the second passageway. The area of the first passageway may be greater than the area of the second passageway. For example, the area of the first passageway may be about 20, 30, 40, 50, 60, 70, or more than 70 percent greater than the area of the second passageway. In other embodiments, the area of the second passageway may be greater than the area of the first passageway. For example, the area of the second passageway may be about 20, 30, 40, 50, 60, 70, or more than 70 percent greater than the area of the first passageway.

The variations in areas of the first and second passageways allows more or less fluid and more or less suction to be administered at the target tissue. For example, in some cases it may be desirable to leave a certain amount of fluid on the target tissue so that the fluid can be slowly absorbed by the tissue. Varying the areas of the first and second passageways allows different fluid volumes, different fluid rates, and different suction amounts at the target tissue to treat the different types of skin conditions that different patients may have.

Figure 5:
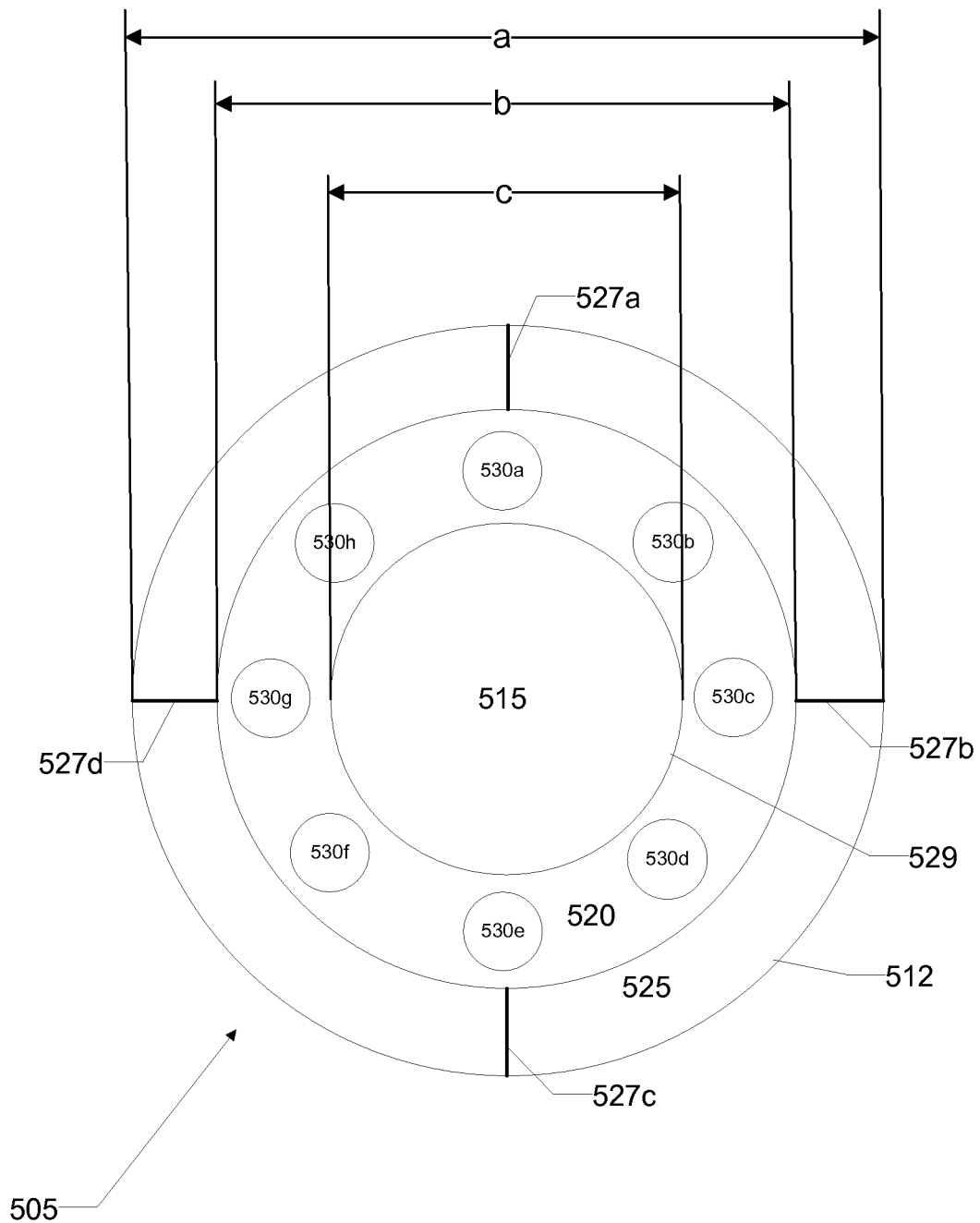
FIG. 5 shows a front view of the first embodiment of a combination microdermabrasion hand piece.

FIG. 5 shows a front view of a hand piece 505. A tip 515 is placed in a tip holder 512. The tip is surrounded by a radiation source holder 520. The radiation source holder is then surrounded by an annular passageway 525. The annular passageway is formed by the inside perimeter of the tip holder and the outside perimeter of the radiation source holder. Support ribs 527a, 527b, 527c, and 527d connect the radiation source holder to the tip holder.

The support ribs extend from an inside edge of the tip holder to an outside edge of the radiation source holder. The support ribs help to form the annular passageway. Generally, the less volume or space taken up by the support ribs enlarges the volume of the annular passageway.

In a specific implementation, fluids exit at an edge 529 of the tip. For example, the tip and tip holder may include one or more channels which mate to form an opening through which fluid flows. The tip may contain a key that fits into a notch in the tip holder. This key and notch feature ensures that the channels in the tip and tip holder are properly aligned to form the fluid openings.

In other implementations, fluids may exit from one or more openings on a surface of the tip. In yet another implementation, the one or more fluid openings may be on or at the end of a nipple placed on the tip. This extends the one or more openings closer to the patient's skin to ensure that the skin is treated with the fluids.

The fluids and abraded tissues are vacuumed or sucked back into the hand piece through the annular passageway. This vacuuming or suctioning of fluids and abraded tissues is the result of a negative pressure condition created in the annular passageway by a vacuum source. The volume of annular passageway will vary depending upon the specific design, but generally, larger volume annular passageways will help prevent potential blockage or other similar problems, especially when compared to pores or other structures that will restrict flow more.

The radiation source holder includes radiation sources 530a, 530b, 530c, 530d, 530e, 530f, 530g, and 530h. The radiation sources may be mounted in the radiation source holder using, for example, an adhesive. The radiation sources are aligned such that they emit radiation into the skin.

In the example shown in FIG. 5, there are eight radiation sources. However, the number of radiation sources can range from one to about fifteen. For example, there may be two, three, four, five, six, seven, eight, nine, ten, eleven, twelve, thirteen, fourteen, or more than fifteen radiation sources.

In a specific implementation, the radiation sources are equally spaced from each other and evenly distributed about tip 515. For example, in an implementation where the radiation sources are arranged in a circle, the angle between any two radiation sources is given by 360 degrees divided by a total number of radiation sources (e.g., for five radiation sources, the angle is 72 degrees; for six radiation sources, the angle is 60 degrees; for seven radiation sources, the angle is 51.4 degrees; for eight radiation sources, the angle is 45 degrees; for nine radiation sources, the angle is 40 degrees). In other implementations, the radiation sources may not be equally spaced from each other.

The example in FIG. 5 also shows each radiation source having the same cross-sectional area. However, this is not always the case. In other implementations, a radiation source will have a cross-sectional area that is different from the cross-sectional area of another radiation source. This may be the case where, for example, the radiation sources include differently sized light emitting diodes. Differently sized light emitting diodes may be used, for example, to provide different amounts of light of a certain wavelength in order to treat a specific skin condition.

Furthermore, the cross-sectional area of the radiation source may not always be the circular cross-sectional area as shown. For example, the cross-sectional area may be another shape such as a square, rectangle, triangle, oval, ellipse, or other. Furthermore, the shape of the cross-sectional area of the radiation source may vary depending on where the cross-section is taken. For example, one end of a radiation source may have a circular shape. The opposite end may have a square shape.

FIG. 5 also shows a specific configuration where the radiation source holder is surrounded by the annular passageway. One advantage of this configuration is that the radiation sources are positioned adjacent to where the fluids exit the tip. This helps to ensure that any light sensitive agents in the fluid will be activated. In an implementation using RF or microwave energy, the configuration also helps to ensure that fluids are present between the radiation sources or electrodes to provide a conductive element and to prevent thermal injury to the skin.

However, other implementations may have different configurations. For example, the radiation source holder may instead surround the annular passageway. This allows, for example, more space to include additional radiation sources to provide a more intense light therapy session. In yet another implementation, another radiation source holder may be present. For example, the annular passageway may be located between a first radiation source holder and a second radiation source holder. The addition of a second radiation source holder may be used to treat a larger surface area of tissue as compared to a single radiation source holder.

Furthermore, in a specific implementation of the invention, there are other radiation sources besides those mounted in the radiation source holder. These other radiation sources, such as LEDs, may not be intended for light therapy. Instead, they may serve other purposes such as illumination, aesthetics, or both. For example, a radiation source may be placed on or near the tip holder and directed at the patient, in order to illuminate the area of skin being treated. This allows a user to easily see the area they are treating as treatments typically occur in dimly lit rooms in order to provide a relaxing environment for the patient. These other radiation sources may also be used for aesthetic purposes. For example, blue LEDs may be placed on the handle to make the hand piece more attractive and contribute to a relaxing ambiance in the treatment room.

FIG. 5 shows a radiation source holder having a ring-like cross-section. However, the specific shape of the radiation source holder may vary. For example, the shape may be a square, rectangle, triangle, oval, ellipse, or other shape.

Several dimensions are also shown in FIG. 5 which are summarized in table A below.

TABLE A

| Variable | First Implementation (mm) | Second Implementation (mm) |
|---|---|---|
| a | 48-88 | 68 |
| b | 32-60 | 46 |
| c | 20-36 | 28 |

It should be appreciated that many other implementations are possible. These dimensions may vary considerably depending on the topography, size, or both of the tissue surface to be treated. For example, the surface area of tip 515 or treatment tip may range from about 25 square millimeters to about 350 square millimeters. A smaller treatment tip (i.e., treatment tip having a small cross-sectional area such as 28.3 square millimeters) may be more suitable for a tissue surface that has many contours, such as a patient's face. The smaller treatment tip can be placed so that it remains flush with the contours of the skin surface during treatment. In other cases, a larger treatment tip (i.e., treatment tip having a large cross-sectional area such as 314 square millimeters) may be more suitable for a large and relatively flat tissue surface, such as a patient's back. The larger treatment tip can cover a greater amount of area and will lessen the treatment time.

In a specific embodiment, a radiation source is within about 20 millimeters of the tip or a diameter or width of tip 515. This facilitates treating of the target tissue (e.g., surface being abraded) with sufficient radiation energy, especially when compared to overhead or ambient background light. The closer the radiation source is to the target surface, the greater the energy level that reaches the target surface; as distance is reduced, the energy increases according a square function. Furthermore, in an implementation, the radiation source is associated with (e.g., attached to the tip), so when the tip moves, the radiation source moves too; as the tip is moved, the distance between the radiation source and the tip does not change. This provides more uniform results (e.g., it is not desirable to have blotchy—such as red spots on some parts of the face—results due to a radiation source distance varying as the tip is used)

For example, one or more radiation sources are within 25.4 millimeters of an abrasive surface of the tip, abrasive brushes of the tip, or vacuum opening of the tip, or any combination of these. In a further implementation, one or more radiation sources are within 10 millimeters of a feature of the tip. In a further implementation, one or more radiation sources are within 5 millimeters of a feature of the tip.

In yet another embodiment, the distance between a radiation source and the tip is less than the longest distance across the tip. The distance between a radiation source and the tip may be less than twice the longest distance across the tip. The longest distance across the tip may vary depending on the shape of the tip. For example, the tip may have the shape of a circle, oval, or ellipse, or polygon. Some examples of polygonal shapes include irregular polygons, regular polygons, squares, rectangles, triangles, pentagons, hexagons, heptagons, octagons, nonagons, decagons, hendecagons, and dodecagons. Furthermore, the shape may be convex or concave (e.g., kidney-shaped and a polygon with a reflex angle).

For example, if the tip has a circular shape then the longest distance across the tip is the diameter of the tip; and the distance between a radiation source and the tip is less than twice the diameter of the tip. If the tip has an elliptical shape then the longest distance across the tip is the major axis of the tip; and the distance between a radiation source and the tip is less than twice the major axis of the tip. If the tip has a triangular shape then the longest distance across the tip is the longest altitude of the tip; and the distance between a radiation source and the tip is less than twice the altitude of the tip.

As a further example, if the tip is a polygon with at least four sides then the longest distance across the tip is the longest diagonal (i.e., the longest distance between nonadjacent vertices). For example, if the tip has a square shape then the longest distance across the tip is the diagonal of the tip; and the distance between a radiation source and the tip is less than twice the diagonal of the tip.

It should also be appreciated that the longest distance across the tip may cross one or more boundary lines of the tip as may be the case with concave shapes. In this case the longest distance across the tip may be the longest line segment between two points on the boundary line of the tip.

In a specific implementation, the tip has a fluid output and a vacuum opening surrounding the tip removes (via suction) the fluid output by the fluid output. However, in other implementations, the fluid flow may operate in reverse; fluid is provided by one or more openings in region 525 and is removed by one or more openings in tip region 515. The radiation source can be between regions 515 and 525.

Figure 6:
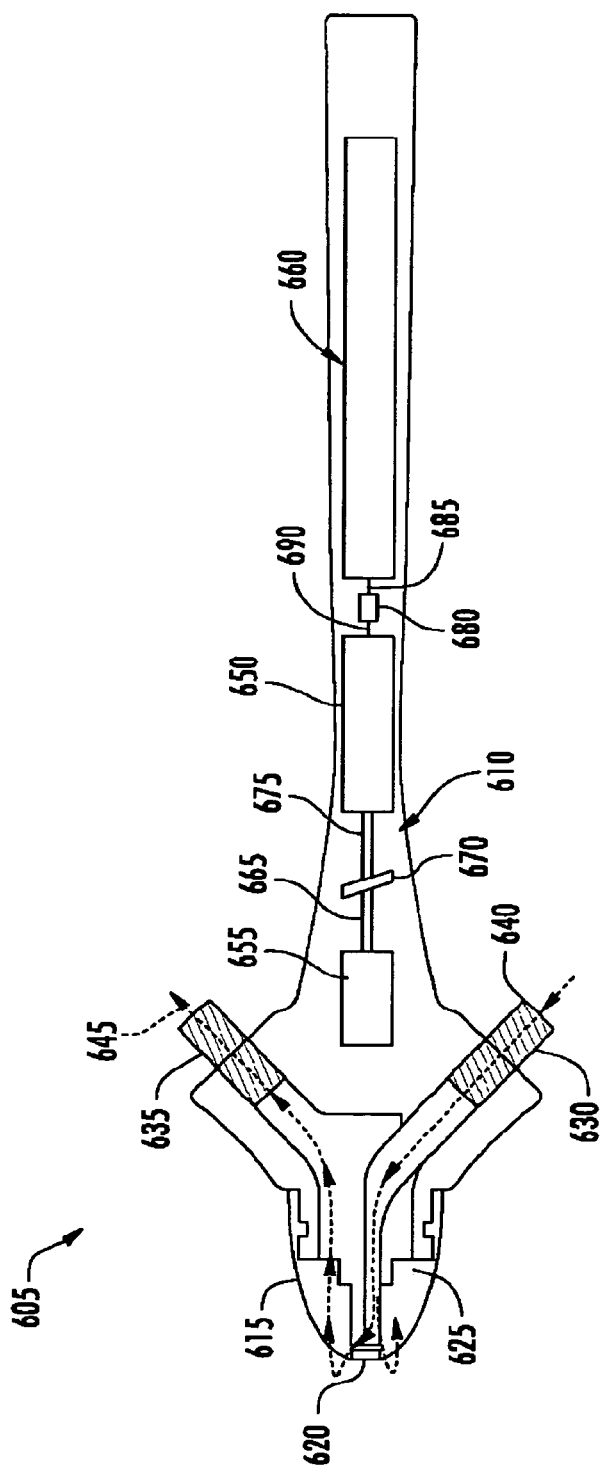
FIG. 6 shows a side view of a second embodiment of a combination microdermabrasion hand piece.

FIG. 6 shows another aspect of the present invention which includes a hand piece 605 that has a vibrating mechanism 610. The hand piece includes a tip holder 615 into which a tip 620 is placed. The tip holder is then fitted over the hand piece to form an annular passageway 625. The hand piece includes a fluid line 630 which is connected to a fluid source. The hand piece includes a vacuum line 635 which is connected to a vacuum source. There is a fluid path 640 and a vacuum path 645 which create a closed loop vacuum. The vibrating mechanism is used to vibrate the tip and tip holder to provide a massage during a microdermabrasion treatment.

In the example shown in FIG. 6, the vibrating mechanism includes a rotary motor 650, an eccentric weight 655, and a power supply 660 to power the rotary motor.

The eccentric weight is attached in an offset position with a rotary shaft 665. The rotary shaft extends from the eccentric weight to a coupler 670. A motor shaft 675 extends from the coupler to the rotary motor. A switch 680 is coupled between the rotary motor and the power supply. The switch has a power input line 685 which is coupled to the power supply. The switch has a power output line 690 which is coupled to the rotary motor.

When the user places the switch into the on position, power flows from the power supply to the rotary motor. The rotary motor then begins to spin the eccentric weight. The rotation of the eccentric weight causes the hand piece to vibrate. The vibrations are transmitted to the tip and tip holder which are placed against the patient's skin. The resulting vibrations can create a pleasant massage effect for the patient. The vibrations may also enhance the movement of the tip over the patient's tissue. That is, the vibrations may be directed to the tip by, for example, coupling the vibrations to a transmitting material that is coupled to or near the tip. Such vibrations may also be used in acoustic therapy.

Certain fluids may be used to enhance the massaging effect. For example, these fluids may carry a warming agent such as eucalyptus, menthol, or ginger root.

In a specific implementation, the power supply is a battery (e.g., triple-A, double-A, C type battery, D type battery). The battery may be disposable or rechargeable. In another implementation, the power may instead be supplied as AC power (e.g., from an AC outlet). When a component, such as the rotary motor uses DC power, the system will include an AC-to-DC converter to convert AC power to DC power.

Although FIG. 6 shows the power supply and the switch within the hand piece, other implementations may have different configurations. For example, the power supply, switch, or both may be located externally to the hand piece such as in a console. A cable (e.g., electrical cable) may then be used to connect the rotary motor in the hand piece to the power supply in the console.

Locating the power supply external to the hand piece may result in a lighter hand piece. This may then result in less fatigue to a user who performs multiple microdermabrasion treatments throughout the day. However, in other cases it may be desirable to place the power supply within the hand piece to result in a heavier hand piece. The additional mass can provide an increased massage effect.

Other embodiments of the invention may use other vibrating mechanisms such as a piezoelectric vibrating device, ultrasonic vibrating device, an ultrasound generator, or other.

Referring now to FIG. 4, in an embodiment, the handle forms a right angle (90-degree angle) to the tip and tip holder. However, in other embodiments, the angle may be different. The angle typically ranges from 0 degrees to about 90 degrees. This includes, for example, 30, 45, 60, or more than 90 degrees. The angle may make the hand piece more comfortable for a user to hold while treating a patient.

The handle may be made of plastic, such as nylon or other plastic, but may also be made of metal, such as stainless steel, for example, or ceramics or composites. The handle may include a combination of materials such as both plastic and rubber. The rubber may be used to provide a surface for the user to grip. The handle may also have a contoured surface. That is, a surface having concave regions, convex regions, or both to make the handle more comfortable to hold.

Although FIG. 4 only shows the hand piece including radiation sources, an embodiment of the invention may also include a vibrating mechanism such as that described above and shown in FIG. 6. Furthermore, the hand piece may contain other electronics to help drive and control the radiation sources such as pulse controllers, capacitors, and the like.

Referring now to FIG. 2A, an embodiment of the invention may include display 234 connected to the control unit via a data line 258. The control unit may also include a security block.

The display may be a flat panel display such as a liquid crystal display (LCD), plasma display, thin film transistor liquid crystal display (TFT LCD), electroluminescent (EL), or organic light emitting diode (OLED) display. The screen may include a touch screen interface. Such touch screen interfaces are easier to clean compared to key pads if they become contaminated because they do not contain mechanical parts.

The display is used to provide information to the user. For example, in an embodiment of the invention using RF energy, or microwave energy, or both, the displayed information may include the temperature of the radiation sources, power level, cycles, or combinations of these. In an embodiment of the invention including LEDs, the displayed information may also include which color LEDs are currently enabled, disabled, or both.

In an embodiment, the control unit includes a security block that controls operation of the system. The security block enables or disables operation of the microdermabrasion system based on certain input (e.g., user input), which varies depending on the specific embodiment of the invention.

When operation is disabled by the security block, the user will not be able to operate the system. For example, the system will not turn on, fluid will not flow, there will be no vacuum, or power is not supplied to one or more components of the system. When enabled, the user will be able to operate the system normally.

For example, the system may include one or more valves placed at various locations on the fluid path, vacuum path, or both. Valves may be placed, for example, between the fluid reservoir and fluid pump, the fluid pump and hand piece, the vacuum source and filter, the filter and the collection reservoir, the filter and collection reservoir, or combinations of these. The security block receives input from various sources and generates a number of signals that goes to various components including the valves. Based on the input, the security block may open the valves to enable operation or close one or more valves to disable the flow path and thus disable operation of the system.

There may also be one or more switches placed on the power path between the security block and the various components that require power such as the fluid pump, vacuum source, radiation sources, microwave generator, or RF generator. The security block may send signals that enable the switches and thus permit power to flow to the components or send signals that disable the switches and prevent power from flowing to the components. Furthermore, in an implementation, a component (e.g., fluid pump, vacuum source, radiation source, microwave generator, RF generator, and negative ion generator) may have a control input which is connected to the security block. This control input controls whether that component turns on or off, even when power is connected to the component.

During a combination microdemabrasion and radiation therapy session, a user places the tip against the patient's skin. As disclosed in U.S. patent application Ser. No. 12/040,867, the tip may be disposable and replaceable and may include abrasive particles or bristles to exfoliate the patient's skin. Fluids flow from the fluid source, through the fluid delivery line and exit the tip. When the vacuum source is turned on, a negative pressure region is created in the vacuum line and around the tip. The negative pressure creates a suction that pulls the patient's skin into contact with the tip. As a user runs the hand piece over the patient's skin, the abraded skin is treated with fluids which are then suctioned away into the hand piece.

Simultaneously, radiation is emitted or outputted from the radiation sources to provide the therapeutic benefits associated with light, photodynamic, RF energy, microwave energy therapy, or combinations of these. This simultaneous blending of therapies offers benefits that are difficult to achieve through, for example, separate microdermabrasion and light therapy treatments. For example, certain fluids may have therapeutic agents that are activated by specific wavelengths of light, heat, or both. Furthermore, the stimulation of the patient's tissue via the suction and abrasion process may allow more infusion and scattering of the light through the tissue than would be the case if the patient's skin was simply exposed to light.

Figure 7:
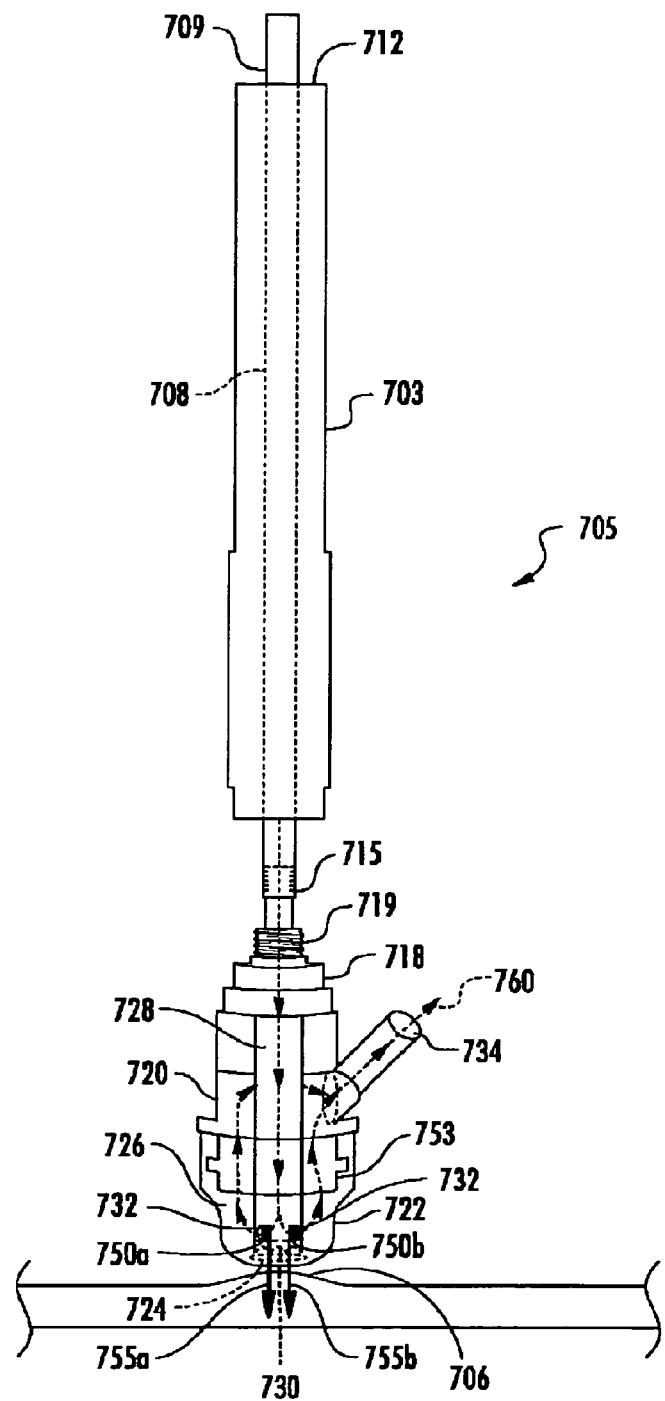
FIG. 7 shows an exploded view of a third embodiment of a combination microdermabrasion hand piece.

FIG. 7 shows a partially exploded view of a specific implementation of a combination microdermabrasion system. This implementation includes a hand piece 705. The hand piece is designed to be handheld by a user for its application to a skin 706 of a patient in the performance of microdermabrasion and radiation therapy. As such, it may be designed with an elongated handle 703 to facilitate grasping by a user. One of ordinary skill in the art will appreciate that many different shapes and materials may be employed for the handle and the present invention is not to be limited to an elongated, substantially cylindrical handle as shown.

One or more radiation sources 750a, 750b are located outside a periphery of an abrasive member or tip 730 (e.g., abrasive region) as in the example of tip 515 in FIG. 5. The radiation sources may be positioned between an annulus 726 and a passageway 728. For example, the radiation sources may be located on a shoulder 753 of a functional block 718. In yet another embodiment, the radiation sources may be located on a treatment tip holder 722. The radiation sources are positioned to emit radiation 755a and 755b into the patient's skin.

In the example of FIG. 7, the handle is made of plastic, such as nylon or other plastic having sufficient toughness and mechanical strength, but may also be made of metal, such as stainless steel, for example, or ceramics or composites. The handle is annular or tubular, providing a passageway 708 through which tube 709 is extended.

Tube 709 is adapted to be connected at its proximal end 712 (the end extending away from handle 703) to a fluid reservoir 226 (see FIG. 2A) which is in turn, open to atmosphere. The tube is flexible and may be made of PVC or other compatible plastic, for example. Similarly, all other vacuum lines described herein are flexible to afford maneuverability to the hand piece and may be made of PVC or other compatible plastic. Alternatively, the proximal end of tube 709 can be left open to atmosphere or connected to a flow control valve, filter, or both, with or without connection to fluid reservoir 226 (see FIG. 2A).

A distal end 715 of tube 709 is connected to functional block 718, by a frictional fit, as shown. Alternatively, a clamp or other type of connector may be provided to facilitate a pressure tight seal between tube 709 and the functional block. The functional block is adapted to be fixed to the handle and may be machined from metal such as surgical stainless steel or may be machined or molded of plastic or casted or molded from ceramic. The functional block may be fixed to the handle using threads 719 or other mechanical or chemical equivalent, although the fixation or interconnection is preferably done so that the functional block can readily be detached and reconnected easily.

A vacuum head base 720 is fitted over functional block 718 to form a pressure tight seal therewith. The vacuum head base may be machined from metal such as surgical stainless steel or may be machined or molded of plastic or casted or molded from ceramic. The vacuum head base may be frictionally fit over the functional block with a seal being effectuated by positioning one or more O-rings or other sealing members between the functional block and vacuum head base 720.

Treatment tip holder 722 is fitted over the end of the vacuum head base, and, likewise may be friction fit, provided with threads, or both or other attachment means to provide a pressure tight fit between the components. The treatment tip holder is smooth surfaced and adapted to glide over the skin surface for application of lotions, vitamins or other fluids thereto during processing. The treatment tip holder may be made of plastic such as nylon or glass, such as Pyrex, for example and is preferably, although not necessarily transparent or translucent. A transparent treatment tip holder allows better visualization by the operator during processing.

One or more O-rings or other sealing members may be provided between vacuum head base 720 and the treatment tip holder to facilitate the pressure tight seal. Alternatively, the treatment tip holder may be integrally machined or molded with the vacuum head base.

The treatment tip holder includes an opening 724 which targets an area of skin to be microabraded when the treatment tip holder is applied to the skin. Although shown with a single large opening 724, it is conceivable that the treatment tip holder could be provided with more than one opening to perform a similar function as described below.

Functional block 718 is a tubular structure that is configured to mate with vacuum head base 720. The vacuum head base is also a tubular structure which has a significantly larger inside diameter than the outside diameter of the distal portion of functional block 718, so as to form an annulus or annular space 726 therebetween. Treatment tip holder 722 extends around annular space 726.

A passageway 728 runs the full length of functional block 718 and forms a continuation of the flow path defined by tube 709 when the tube is connected to the proximal end of functional block 718.

An abrasive member or tip 730 is formed at the distal end of functional block 718 thereby closing off passageway 728 at the distal end of functional block 718. The abrasive member is formed by fusing abrasive particles to the end of the functional block 718, or could alternatively be made as an abrasive disk and fitted within an open end of the functional block to seal the end or mounted to a closed end of functional block 718. Although the abrasive member shown is substantially planar, it may alternatively be rounded, flared, concave, convex or elongated, for example. The abrasive particles are of a size ranging from about 50 grit to 300 grit, typically about 100 grit to 120 grit and are typically carborundum (aluminum oxide) or sodium bicarbonate, or the like. The coarser particles (at the lower ends of the grit ranges) may be provided on a functional block for use in initial treatments, while finer particles (at the higher ends of the grit ranges) may be employed for subsequent treatments.

Alternatively, the abrasive member may be formed by knurling, machining, laser treatment or otherwise mechanically or chemically treating a closed end of the functional block to form the abrasive end. One or more openings 732 are provided through the wall of the distal tubular structure of functional block 718 to establish one or more flow pathways between passageway 728 and annulus 726. Treatment tip holder 722 extends beyond the extremity of functional block 718 such that abrasive member 730 is positioned internally of assembled hand piece 705, and surrounded by annulus 726.

An opening or port 734 is provided in the vacuum head base 720 for connection of a vacuum source, for example, by connecting vacuum port 734 to the vacuum source via a vacuum line. When vacuum is applied through opening 734, opening 724 is sealed off, for example, by placing it up against skin tissue, a closed loop vacuum flow path is established between the vacuum source and connecting line, vacuum opening 734, annulus 726, one or more openings 732, passage way 728, and tube 709. This flow path is shown in FIG. 7 as a dotted line 760.

Figure 8:
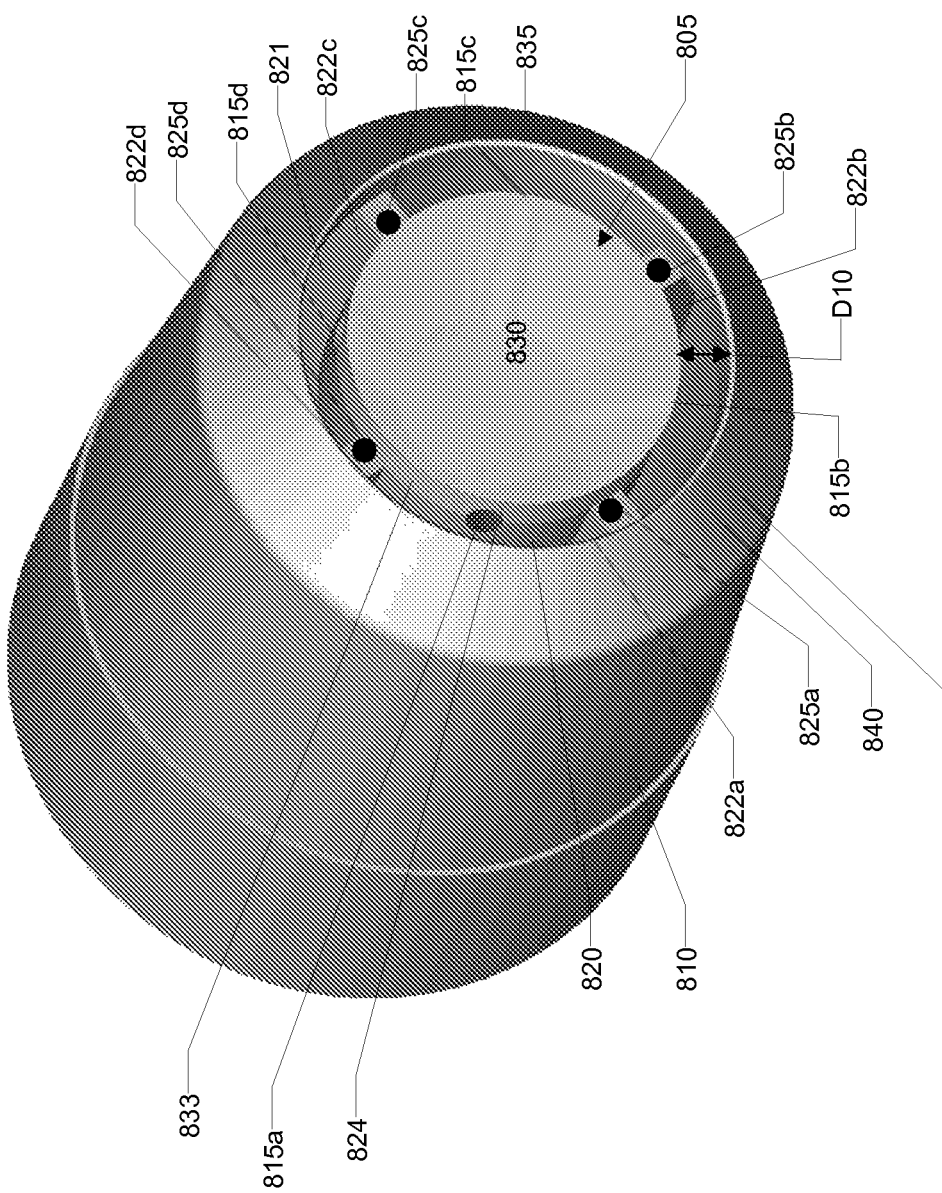
FIG. 8 shows a front view of an embodiment of a tip holder and abrasive tip.

FIG. 8 shows an example of an abrasive tip 805 placed within a tip holder 810. The tip holder may include one or more radiation sources such as radiation sources 825a, 825b, 825c, and 825d. Fluid flows out of one or more fluid openings such as fluid openings 815a, 815b, 815c, and 815d to treat the skin. An annular opening 820 surrounds the abrasive tip and fluid openings. The annular opening is connected to an annular passageway 821. Support ribs, such as 822a, 822b, 822c, and 822d help to support tube 823 in the annular passageway.

As shown in the example in FIG. 8, a fluid opening includes an outer edge 824 at a first position which is outside an edge or periphery 840 of the abrasive surface. The fluid input opening (i.e., annular opening) includes an edge or outer edge 843 at a second position, outside a periphery of the abrasive surface and is a greater distance away from the abrasive surface than the second position.

Figure 10:
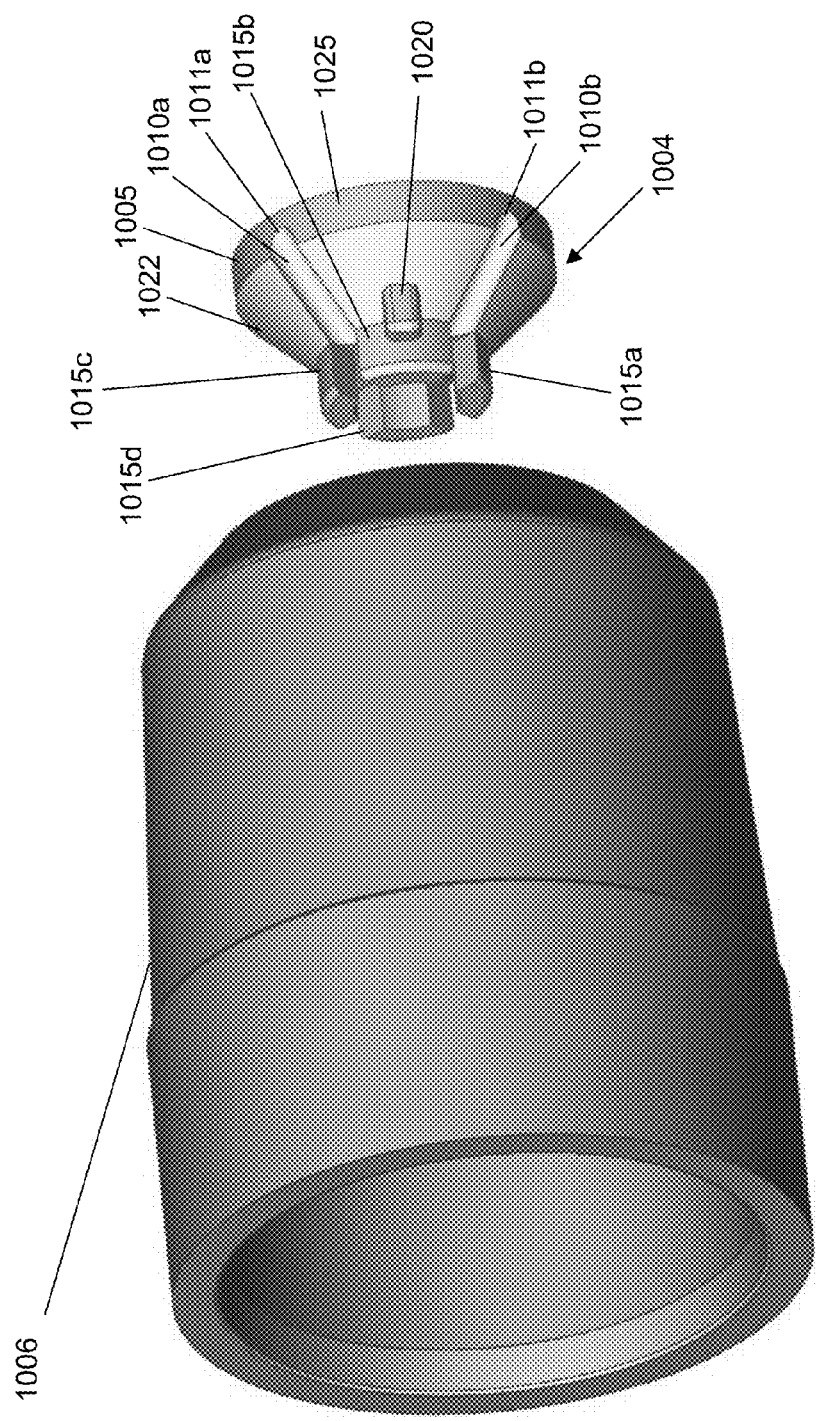
FIG. 10 shows a back view of an embodiment of the tip.

In a specific implementation, the abrasive tip includes an abrasive surface 830, a side surface 833, and a back side 1004 (see FIG. 10). An edge 840 at the perimeter of the abrasive surface and an edge 843 of the tip holder form the annular opening. That is, edge 840 defines an inner edge and edge 843 defines an outer edge. The annular opening is the region between the inner and outer edges. In an embodiment, the inner and outer edges are concentric circles. That is, edge 840 (i.e., inner edge) is the inner circle and edge 843 (i.e., outer edge) is the outer circle.

Side surface 833 and an inner surface 835 of the tip holder form the annular passageway. Fluids and abraded tissues are vacuumed or suctioned back into the wand or hand piece through the annular passageway. That is, a negative or low pressure region relative to ambient pressure is created in the annular passageway.

In a specific embodiment, the annular opening is on the same plane as the abrasive surface. However, in other embodiments, the annular opening is below or above the plane of the abrasive surface. For example, the annular opening may range from about 0.5 millimeters to about 5 millimeters above or below the plane of the abrasive surface.

The annular opening includes a surface area A10. Surface area A10 is generally calculated by noting that a distance D10 is between edge 840 of the abrasive tip and edge 843 of the tip holder. That is, D10 indicates a width of the annular opening. In a specific embodiment where the abrasive surface and tip holder have circular cross sections, surface area A10 can be calculated using the equation below:

$$A10 = \pi \left[ \frac{\text{Diameter of abrading surface} + (2*D10)}{2} \right]^2 - \pi \left[ \frac{\text{Diameter of abrading surface}}{2} \right]^2 \quad (1)$$

For example, in a specific embodiment, the diameter of the abrasive surface is about 9 millimeters and distance D10 is about 1.5 millimeters. Inserting these values in to equation (1) results in a value of about 49 square millimeters for surface area A10. In this specific embodiment, surface area A10 is less than the surface area of the abrasive surface which is about 64 square millimeters. Surface area A10 is about 23 percent less than the surface area of the abrasive surface, but may range from about 15 percent to about 30 percent less.

However, in other embodiments, surface area A10 of the annular opening is greater than the surface area of the abrasive surface. For example, in a specific embodiment, the diameter of the abrasive surface is about 6 millimeters and distance D10 is about 1.5 millimeters. Inserting these values into equation (1) results in a value of about 36 square millimeters for surface area A10. In this specific embodiment, surface area A10 is greater than the surface area of the abrasive surface which is about 28 square millimeters. Surface area A10 is about 28 percent greater than the surface area of the abrasive surface, but may range from about 15 percent to about 40 percent greater.

Generally, a larger surface area A10 of the annular opening or a larger distance D10 is desirable. This will help prevent potential blockage or other similar problems. That is, a larger surface area A10 or distance D10 allows fluid and other debris such as abraded skin particles to pass through without becoming wedged in the annular opening.

As discussed, in a specific embodiment, distance D10 is about 1.5 millimeters. But distance D10 may range from about 0.5 millimeters to about 10 millimeters. This includes, for example, 0.6, 0.7, 0.8, 0.9, 1, 1.1, 1.2, 1.3, 1.4, 1.5, 1.6, 1.7, 1.8, 1.9, 2, 2.5, 3, 3.5, 4, 4.5, 5, 6, 7, 8, 9, 10, or more than 10 millimeters, and less than 0.5 millimeters.

Distance D10 varies depending on the specific design or application. For example, in some cases a patient may have very dry and flaky skin. A microdermabrasion treatment for this particular patient may result in large pieces of skin being removed. Thus, a microdermabrasion wand with a large annular opening (e.g., large distance D10) will help to prevent the annular opening from becoming clogged with the large pieces of skin. As another example, a different patient may have normal skin that does not include flaky areas. In this case, a microdermabrasion wand with a smaller annular opening (e.g., smaller distance D10) may be used.

The abrasive tip or abrasive surface of the abrasive tip is typically made of an impermeable material that does not permit fluid (e.g., gas, air, and liquids) to flow or pass through. That is, the material is generally not a sponge or pad. In other words, in a specific embodiment, fluid from a fluid opening is placed on the abrasive surface without passing through the abrasive surface.

The abrasive tip is typically solid and may be made of, for example, plastics such as nylons, thermoplastics, polyethylene, polycarbonate, acrylonitrile butadiene styrene (ABS), metals such as stainless steel, aluminum, titanium, or brass.

Because the abrasive tip is typically designed so that fluid flows around it or through channels within it, there is less of a chance that the fluid flow will be restricted as compared to other materials such as sponges, pads or other membranes. In these other materials, fluid flows through small pores in the material and these small pores are more likely to become clogged.

The abrasive surface is generally formed by fusing (e.g., gluing and imbedding) abrasive particles to the surface. Examples of abrasive particles include diamond, silicone carbide, magnesium oxide, aluminum oxide, and the like, or combinations of these. The abrasive surface may also be formed by applying an adhesive-backed paper substrate to the surface, knurling, machining, laser treatment or otherwise mechanically or chemically treating the surface. The abrasive surface may also include an abrasive open screen with bonded abrasive particles.

Some embodiments of the abrasive tip include porous materials. For example, in a specific embodiment of the abrasive tip, the abrasive tip includes an abrasive mesh or web.

The side surface is at an angle to the abrasive surface. In a specific embodiment, the side surface is at a 90-degree angle (i.e., perpendicular) to the abrasive surface. One or more fluid openings (815a-d) are at least partially formed on the side surface. There can be any number of fluid openings. For example, there may be one fluid opening, two fluid openings, or three or more fluid openings such as four fluid openings as shown in the example of FIG. 8. In a specific embodiment, these fluid openings are evenly distributed around the abrasive tip. For example, an angle between the fluid openings is given by 360 degrees divided by the total number of fluid openings (e.g., two fluid openings, the angle is 180 degrees, three fluid openings, the angle is 60 degrees, four fluid openings, the angle is 90 degrees; and for five fluid openings, the angle is 72 degrees).

Since the side surface is at an angle to the abrasive surface, these fluid openings may also be at an angle relative to the abrasive surface. For example, the fluid openings may be perpendicular to the abrasive surface as shown in the example in FIG. 8. In other words, a line passing through the perimeter of a fluid opening intersects a plane on which the abrasive surface lies.

One benefit of this orientation of the fluid openings to the abrasive surface is that there is less of a chance that the fluid openings will become blocked by the tissue surface. The fluids exit from the fluid openings, into the annular passageway, and out the annular opening. The fluids are free to flow directly to the skin without having to first flow through any sponge, pad, or other membrane or porous material. For example, during use, the abrasive surface contacts the skin surface. At this point, the skin surface and abrasive surface all lie on the same plane. The fluid openings, however, are at an angle to that plane and are thus unlikely to become blocked by the skin surface. The fluid then flows back into the annular opening and into the annular passageway.

As another feature, fluid deposited on the abrasive surface from a single fluid opening is capable of being drawn into the annular opening from one, two, three or more than three directions. Two or more directions may be opposite to each other, transverse to each other, or both. For example, as the user runs the abrasive tip over the patient's skin, fluid exits from the fluid openings such as fluid opening 815a. The suction in the annular opening and the movement of the tip across the skin surface allows the fluid or a portion of the fluid to flow across or spread out over the abrasive surface and treat the target skin. The fluid can then be drawn into the annular opening. In some cases, the fluid exiting fluid opening 815a will travel the furthest distance across the tip (e.g., diameter of a circular tip and diagonal of a square or rectangular tip) before being drawn into the annular opening. In other cases, the fluid exiting fluid opening 815a will travel a shorter distance across the tip (e.g., cord of a circular tip and side of a square or rectangular tip).

Furthermore, this orientation allows the fluid flow to operate independently of the force that the user applies to the hand piece. For example, if the user applies a large amount of force to the hand piece to produce a large amount of abrasion, the fluid openings will not become blocked or constricted and fluid will continue to freely flow and treat the skin. For example, the fluid openings will not become smaller or compressed since the fluid openings are formed from rigid materials (e.g., plastic).

Although FIG. 8 shows the annular opening, passageway, and tube having circular shapes, other embodiments have different shapes or combinations of different shapes. Some examples of other shapes include squares, rectangles, ovals, and triangles.

Figure 9:
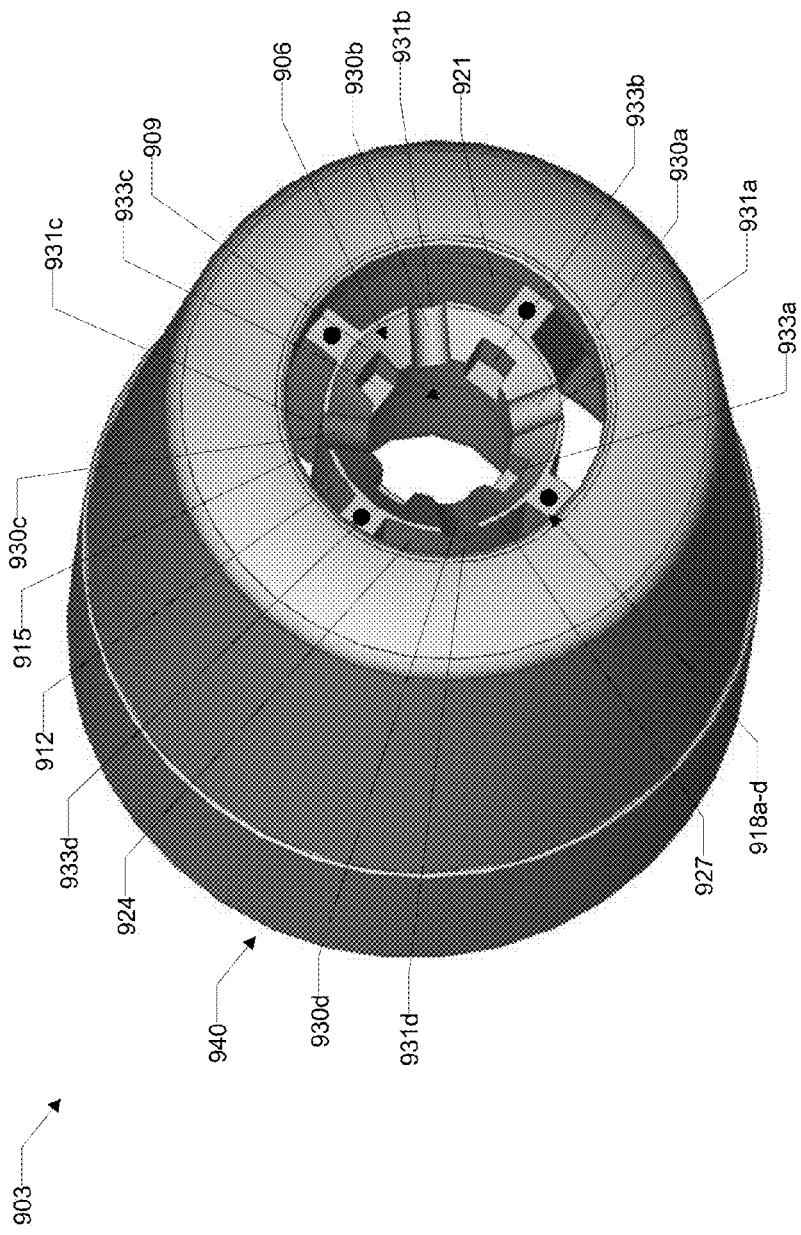
FIG. 9 shows a front view of an embodiment of the tip holder.

FIG. 9 shows a front view of a specific implementation of a tip holder 903 that includes a recess 906 at a distal end 909 of a tube 912. The tube includes an opening at its distal end. The opening can be referred to as a fluid channel opening or a first fluid channel opening. An abrasive tip fits into the recess. The tube is surrounded by an annular space or passageway 915. The annular passageway may be interrupted by one or more support ribs 918a-d which span from an inner surface 921 of the tip holder to an outer surface 924 of the tube.

The recess includes a surface 927 which in turn includes features that help position the abrasive tip and direct fluid flow around the abrasive tip. Typically, the abrasive tip is positioned such that it is centered on the tube. For example, a longitudinal axis passing through the center of the tube will also pass through a center of the abrasive tip. However, in other embodiments, the abrasive tip is offset from the tube.

The features that help position the abrasive tip and direct fluid flow around the tip include one or more channels such as channels 930a, 930b, 930c, and 930d. The channels include channel openings 931a, 931b, 931c, and 931d. These channel openings can be referred to as fluid channel openings or second fluid channel openings. These features also include one or more notches such as notches 933a, 933b, 933c, and 933d.

There may be any number of channels (e.g., no channels, one, two, three, four, five, or more than five channels). In an embodiment, the channels are evenly distributed about a lumen 936 of the tube. For example, an angle between the channels is given by 360 degrees divided by the total number of channels openings (e.g., two channels, the angle is 180 degrees, three channels, the angle is 60 degrees, four channels, the angle is 90 degrees; and for five channels, the angle is 72 degrees).

The channels in the recess align with channels in the abrasive tip to form the fluid openings. The notches in the recess help to position the abrasive tip so that the fluid openings can be formed. That is, the notches mate with keys on the abrasive tip.

In an embodiment, the surface of the recess is at an oblique angle relative to the outer surface of the tube. Typically, that angle is an acute angle. This allows fluid to flow through the lumen of the tube and out the distal end where the fluid is divided via the channels and directed along the channels and to a periphery of the abrasive tip. The fluid is then vacuumed or suctioned into the annular passageway.

The tube is positioned within the annular passageway. In a specific embodiment, the tube and annular passageway are positioned to form concentric circles. That is, the tube and annular passageway share a common center axis and the annular passageway encircles the abrasive surface. For example, a lateral cross section through the tip holder shows an inner circle (i.e., tube) and an outer circle (i.e., annular passageway) having a diameter that is greater than the diameter of the inner circle (i.e., tube). The inner and outer circles are concentric. A fluid flow is through the tube, through the fluid openings, into the annular passageway, out the annular opening, and then back into the annular opening and annular passageway. In other words, fluids pass out of and back into the same opening, i.e., the annular opening.

In this specific embodiment, the pressure in the lumen of the tube is greater than the pressure in the annular passageway. That is, the annular passageway includes a region of pressure which at least partially surrounds the tube. The region of pressure is less than the pressure in the lumen of the tube. This pressure differential at least partially contributes to the fluid flow through the lumen of the tube, out the distal end of the tube, and then back into the hand piece through the annular passageway.

In another embodiment, the fluid flow is reversed. That is, fluid flows through and out the annular passageway and then flows into the lumen of the tube.

In a specific embodiment, the fluid in the lumen is a liquid rather than a gas. That is, the fluid is incompressible. However, in other embodiments, the fluid includes gases as well.

The tip holder may be designed so that the abrasive tip can rest or sit on the tip holder. Specifically, the abrasive tip may rest or sit on the recess of the tip holder rather than being placed between the tip holder and some other member of the microdermabrasion hand piece. This makes the abrasive tip easy to replace since it allows the user to remove the abrasive tip and insert a new abrasive tip without having to also remove the tip holder. However, in other implementations, as shown, for example, in FIG. 11, the abrasive tip is placed between the tip holder and another member of the microdermabrasion hand piece.

It should be appreciated that any arrangement or number of support ribs (including no support ribs) is possible so long as fluids are able to pass through the vacuum created in the annular passageway.

Consequently, a flange, or a portion of a flange may be used between the inner surface of the tip holder and the outer surface of the tube, either with or without support ribs. For example, where a flange completely encircles the tube, the flange may contain one or more openings which allow fluids to pass from the front of the tip holder to the back of the tip holder.

The tip holder may be formed using any number of manufacturing techniques. Some examples include machining, casting, molding, injection molding, etching, or combinations of these.

In a specific embodiment, the outer width (e.g., outer diameter) of the tip holder tapers or decreases from a proximal end 940 of the tip holder to the distal end of the tube. This may also result in a tapering or decrease of the cross-sectional area of the annular passageway from proximal end 940 to the distal end of the tube. However, in other embodiments the cross-sectional area of the annular passageway remains constant regardless of whether the outer diameter of the tip holder tapers. For example, the walls of the tip holder may have a thickness that varies. The walls of the tip holder may be thicker at the proximal end of the tip holder than at the distal end of the tube. Thus, a cross-sectional area taken at a point between the proximal and distal ends may be the same as a cross-sectional area taken at a different point between the proximal and distal ends.

FIG. 10 shows a view of the back side of a specific implementation of an abrasive tip 1005 that fits into a tip holder 1006. In this implementation, the abrasive tip 1005 includes channels 1010a, 1010b, 1010c, and 1010d. The channels include channel openings 1011a, 1011b, 1011c, and 1011d. These channel openings can be referred to as fluid channel openings or third fluid channel openings. Channels 1010c and 1010d and channel openings 1011c and 1011d are not shown due to the perspective view of the drawing. Abrasive tip 1005 also includes collars 1015a, 1015b, 1015c, and 1015d and a key 1020.

In a specific implementation, the channels 1010a, 1010b, 1010c, and 1010d are equally spaced around the perimeter of the abrasive tip. For example, in an implementation where the abrasive tip has a circular cross section and four channels, the channels may be located at 0, 90, 180, 270, and 360 degrees. In other implementations, the abrasive tip may include less than four channels, such as no channels, one channel, two channels, or three channels. In another implementation, there may be more than four channels, including, for example, five, six, seven, eight, or more than eight channels.

The channels are recessed into a conical surface 1022 on the back side of the abrasive tip. An angle between the conical surface and the abrasive surface is typically less than 90 degrees. For example, the angle may range from about 20 degrees to about 80 degrees. This includes less than 20 degrees, 30, 40, 45, 50, 60, 70, or more than 80 degrees. The conical surface starts at the cylindrical surface of the collars and spreads out towards the front of the abrasive tip. The channels extend outwardly through the collars towards the front of the abrasive tip. In a specific implementation, the channels terminate on a side surface 1025 of the abrasive tip. In another implementation, the channels may continue through to the front of the abrasive tip.

Channels 1010*a*, 1010*b*, 1010*c*, and 1010*d* in the abrasive tip align with channels 930*a*, 930*b*, 930*c*, and 930*d* in the tip holder as shown in FIG. 9. When these channels are aligned they form the openings 815*a*, 815*b*, 815*c*, and 815*d* as shown in FIG. 8 that fluid flows out of. For example, with reference to FIGS. 8, 9, and 10, channel 1010*a* in the abrasive tip aligns with channel 930*a* in the tip holder to form opening 815*a*. Channel 1010*b* in the abrasive tip aligns with channel 930*b* in the tip holder to form opening 815*b*. Channel 1010*c* in the abrasive tip aligns with channel 930*c* in the tip holder to form opening 815*c*. Channel 1010*d* in the abrasive tip aligns with channel 930*d* in the tip holder to form opening 815*d*.

FIG. 10 shows U-shaped or semi-circular shaped channels which, when aligned, form circular shaped openings. However, this is not always the case. In other implementations, the openings formed may have the shape of a polygon such as a rectangle or square, or the shape may be elliptical or oval. Furthermore, there may be a combination of differently shaped openings which are formed using differently shaped channels.

In a specific implementation, the openings allow fluid to flow out around the perimeter of the abrasive tip as opposed to the front surface of the abrasive tip. This prevents the tissue that is being treated from occluding the openings.

However, in other implementations, there may be openings on the surface of the abrasive tip itself. For example, there may be an opening for fluid located in the center of the abrasive tip. Additionally, there may also be a combination of openings at different locations. For example, there may be openings located at or near the perimeter of the abrasive tip and an opening or openings on the surface of the abrasive tip.

In a specific implementation, the openings all have the same cross-sectional areas. The total cross-sectional area of the openings is less than the surface area of the abrasive surface. For example, the total cross-sectional area of the opening may be about 20 to about 60 percent less than the surface area of the abrasive surface.

Each cross-sectional area of an opening may range, for example, from about 0.05 square millimeters to about 20 square millimeters. For example, the cross-sectional areas may be 0.06, 0.07, 0.08, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.5, 4, 4.5, 5, 10, 15, or 19.9 square millimeters. Depending on the application, the cross-sectional area may be less than 0.05 square millimeters, or greater than 20 square millimeters. In other implementations, the cross-sectional areas of the openings will be different. For example, one opening may have a cross-sectional area of 0.03 square millimeters, while another opening may have a cross-sectional area of 0.05 square millimeters.

In yet another implementation, the cross-sectional area of a particular opening may vary from one end of the opening to the opposite end. This allows, for example, varying the flow rate and velocity of fluid exiting from the openings.

In a specific implementation, key 1020 in the abrasive tip fits into any of notches 933*a*, 933*b*, 933*c*, and 933*d* in the tip holder as shown in FIG. 9. Thus, this specific implementation provides for four different positions for the abrasive tip to be positioned in tip holder.

There may be any number of keys. For example, there may be no keys, one, two, three, four, five, or more than five keys. In a specific implementation, the number of keys on the abrasive tip is the same as the number of notches on the tip holder. In another implementation, the number is different. For example, there may be fewer keys on the abrasive tip than notches on the tip holder.

In a specific implementation, the sizes of the keys and notches are the same. In another implementation, the sizes are different. In yet another implementation, the notches are on the abrasive tip while the keys are on the tip holder, or there may be a combination arrangement. That is, an implementation includes a combination of keys and notches on both the abrasive tip and tip holder.

The key or keys ensure that channels 930*a*, 930*b*, 930*c*, and 930*d* in the tip holder (see FIG. 9) and channels 1010*a*, 1010*b*, 1010*c*, and 1010*d* in the abrasive tip are properly aligned to form openings 815*a*, 815*b*, 815*c*, and 815*d* (see FIG. 8) through which fluid flows out.

In a specific implementation, the keys are used to specifically misalign certain channels in the tip holder and abrasive tip in order to not form an opening for fluid to exit. Thus, the amount of fluid exiting may be adjusted by misaligning the channels in the abrasive tip with the channels in the tip holder.

In a specific implementation where there is a particular direction of travel for the abrasive tip, the keys may also be used to ensure that the abrasive tip is properly positioned along the particular direction of travel. For example, the abrasive tip may include two regions having different grits such as coarse and fine grits. A microdermabrasion treatment may include treatment with the coarse grit followed by the fine grit. Thus, the user will run the hand piece over the patient's tissue so that the tissue is first treated by the coarse grit region of the abrasive tip.

Collars 1015*a*, 1015*b*, 1015*c*, and 1015*d* slide into the tip holder. Collars 1015*a*, 1015*b*, 1015*c*, and 1015*d* are positioned between channels 1010*a*, 1010*b*, 1010*c*, and 1010*d* in the abrasive tip. This allows fluid to flow out of the openings formed by aligning the channels in the abrasive tip with the channels in the tip holder. The collars protrude from the back side of the tip.

The number of collars may vary. Typically, the number of collars will be dependent on the number of channels. For example, if there are four channels, then there will be four collars. However, this is not always the case. In other implementations, the number of collars will be different from the number of channels. There may be more channels than collars, or there may be fewer channels than collars.

Figure 11:
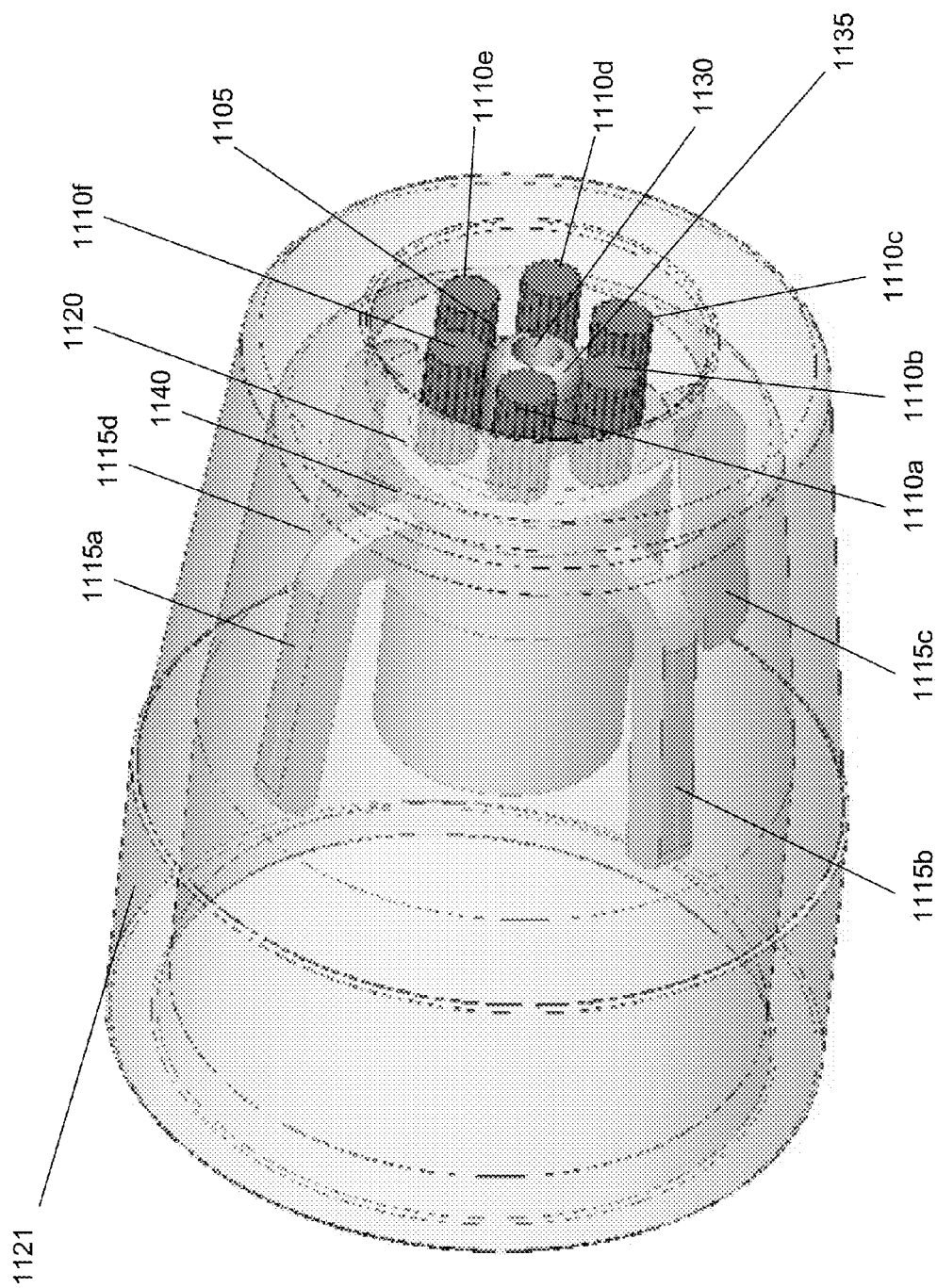
FIG. 11 shows an embodiment of a bristled tip.

FIG. 11 shows an example of a specific implementation of a bristled tip 1105. In a specific implementation, bristled tip 1105 may have six groups of bristles (1110*a*, 1110*b*, 1110*c*, 1110*d*, 1110*e*, 1110*f*), four support ribs or prongs (1115*a*, 1115*b*, 1115*c*, 1115*d*) which are offset from a face 1120 of the bristled tip, and an opening 1130 which is at the end of a nipple 1135.

In one embodiment, one or more bristles may be coupled to a radiation source. For example, the bristle may be coupled to an LED. The bristle may act as a waveguide for directing radiation from the radiation source and into the tissue. Thus, in a specific implementation, the bristle may be made of optical fiber.

In yet another embodiment, one or more bristles may be translucent so that the bristles do not block any light that may be transmitted from the radiation sources into the patient's tissue. Thus, in specific embodiments, light is transmitted through an area of tissue that is being abraded.

Although FIG. 11 shows six groups of bristles, the number of groups of bristles may vary. For example, other implementations may have one, two, three, four, five, or more than six groups of bristles.

Nipple 1135 extends some distance away from face 1120 of the bristled tip. The opening may extend from about 30 percent to about 75 percent the length of the bristles, including, for example, less than 30 percent, 50 percent, or more than 75 percent the length of the bristles.

In an implementation, fluid flows through the nipple and out the opening. The nipple places opening 1130 closer to the skin and helps to ensure that the fluid contacts the skin before being pulled back into a tip holder 1121.

Support ribs or prongs 1115*a*, 1115*b*, 1115*c*, and 1115*d* may be offset from face 1120 of the bristled tip and attached at any point along the length of the bristled tip. In a specific implementation, the distance for the offset is the same for all support ribs 1115*a*, 1115*b*, 1115*c*, and 1115*d*. In other implementations, the support ribs may be offset at different distances. For example, support rib 1115*a* may be offset from face 1120 by 0.5 millimeters, while support ribs 1115*a*, 1115*b*, and 1115*c* may be offset from face 1120 by 1 millimeter.

Offsetting the support ribs allows, for example, an uninterrupted annular space 1140 to be created near the front of the tip holder 1121. This allows fluids to more easily pass back into tip holder 1121 without being blocked by any structures. However, other implementations may have the support ribs or prongs flush with face 1120.

The support ribs or prongs extend outwardly and then turn to splay longitudinally down the length of the bristled tip.

Although FIG. 11 shows four prongs, the number of prongs may vary. For example, other implementations may have one, two, three, five, six, seven, or more than eight prongs.

It should be appreciated that there may be many different combinations of bristled tips that include, for example, different numbers of bristle groups, support ribs and fluid openings, different attachment positions for support ribs, or different positions for fluid openings. For example, in a specific implementation, the bristled tip may include three support ribs flush with face 1120 and six groups of bristles. In another configuration, the support ribs may not be equally spaced from each other. For example, instead of being spaced at 0 degrees and 180 degrees, the support ribs may be spaced at 0 degrees and 92 degrees. Furthermore, a first support rib may be attached flush with the face of the bristled tip while a second support rib is offset 0.5 millimeters, for example, from the face of the bristled tip.

A specific flow example of invention shown in FIG. 2A is presented below. However, it should be understood that the invention is not limited to the specific flows and steps presented. A flow of the invention may have additional steps (not necessarily described in this application), different steps which replace some of the steps presented, fewer steps or a subset of the steps presented, or steps in a different order than presented, or any combination of these. Further, the steps in other implementations of the invention may not be exactly the same as the steps presented and may be modified or altered as appropriate for a particular application or based on the data or situation.

1. The user places the hand piece with the abrasive tip against the patient's skin and turns on the system.
2. Power is sent from the control unit to the fluid pump and vacuum source.
3. Fluid begins to flow through fluid delivery line 214 where it exits the tip and contacts the patient's skin.
4. The fluid is then suctioned back into hand piece via vacuum line 216.
5. The user enables switch 240 which sends power to the radiation sources.
6. The radiation sources transmit radiation (e.g., red light, blue light, and yellow light) into the patient's skin.
7. The user runs the hand piece over the patient's skin. The abrasive tip loosens the dead skin cells while fluids provide a pre and post treatment of the abraded area before being suctioned away. Meanwhile, the radiation sources direct therapeutic radiation into the treatment site.

A specific flow example of invention shown in FIG. 6 is presented below. However, it should be understood that the invention is not limited to the specific flows and steps presented. A flow of the invention may have additional steps (not necessarily described in this application), different steps which replace some of the steps presented, fewer steps or a subset of the steps presented, or steps in a different order than presented, or any combination of these. Further, the steps in other implementations of the invention may not be exactly the same as the steps presented and may be modified or altered as appropriate for a particular application or based on the data or situation.

1. The user places the hand piece with the abrasive tip against the patient's skin and turns on the system.
2. Power is sent from the control unit to the vacuum source. The vacuum source creates a negative pressure condition in the fluid reservoir which sucks the fluid from the fluid reservoir into the fluid delivery line.
3. The fluid exits the tip and contacts the patient's skin.
4. The fluid is then suctioned back into the hand piece via vacuum line 216.
5. The user enables switch 680 to start the massage. Power is then supplied via the power source to the rotary motor.
6. The user runs the hand piece over the patient's skin. The abrasive tip loosens the dead skin cells while fluids provide a pre and post treatment of the abraded area before being suctioned away. Meanwhile, the rotary motor creates a vibration at the tip and tip holder. The effect is a massaging of the treatment site. The massage helps to further abrade the skin while relaxing the tissue at the treatment site.

Figure 12:
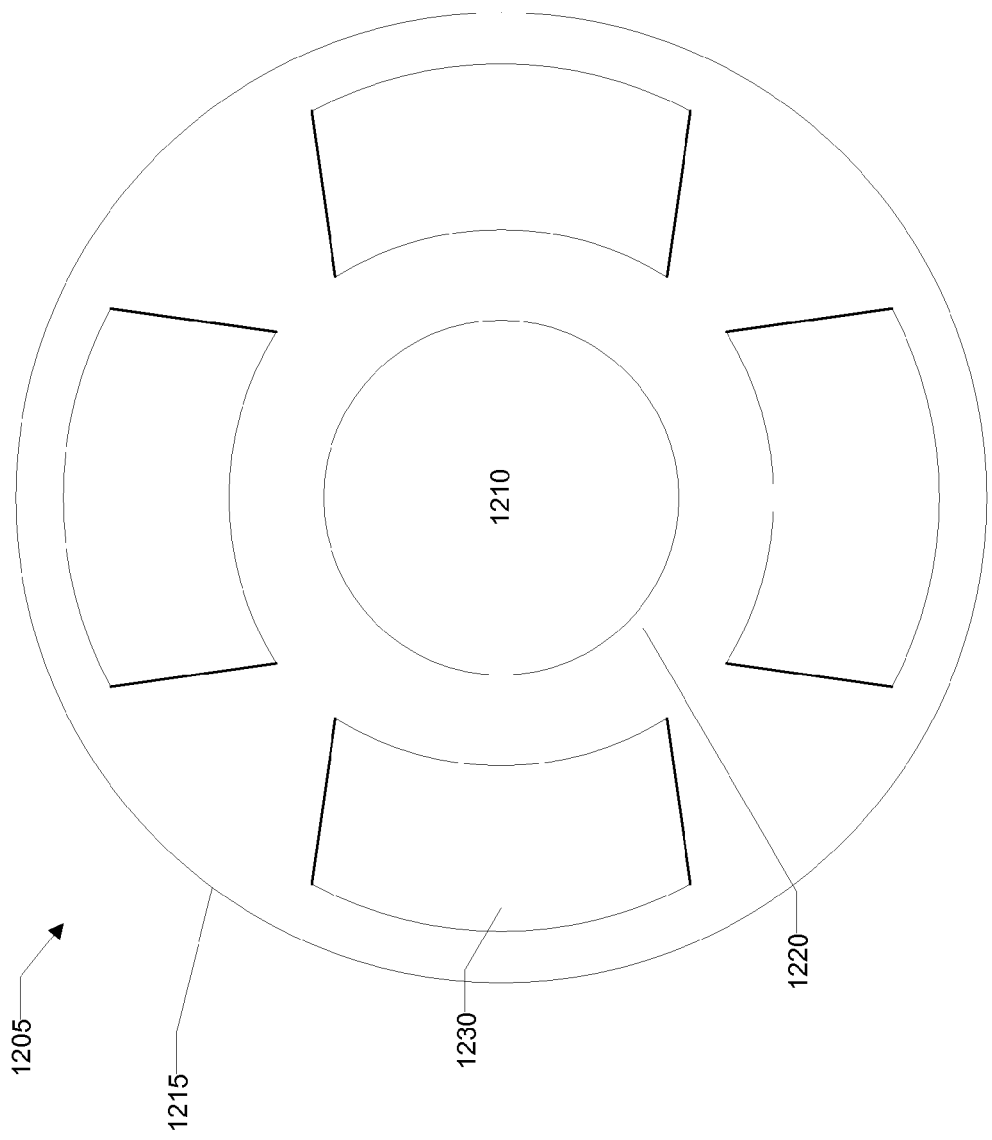
FIG. 12 shows a front view of an embodiment of a hand piece with an arc-shaped vacuum opening.

FIG. 12 shows a partial front view of another embodiment of a hand piece 1205 including a tip 1210 and a tip holder 1215. One or more fluid openings 1220 are positioned outside a periphery 1225 of the abrasive tip. The fluid openings output fluid. One or more vacuum openings 1230 are also positioned outside the periphery of the abrasive tip and are positioned at a further distance away from the abrasive tip than the fluid output openings.

As shown, the vacuum openings are at least partially around the abrasive tip. The vacuum openings may be connected to one or more vacuum lines. Although FIG. 12 shows the vacuum openings as having arc shapes, other embodiments may include differently shaped vacuum openings such as square, rectangular, circular, oval, or triangular openings.

In other embodiments, the fluid flow is reversed. That is instead of fluid opening 1220 outputting fluid and vacuum opening 1230 inputting fluid, fluid opening 1220 accepts fluid input and vacuum opening 1230 outputs fluid.

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

The invention claimed is:

1. A microdermabrasion system comprising:
a console; and
a hand piece comprising:
- a tip, coupled to a fluid tube coupled to the console, wherein the tip comprises an abrading surface formed on a front surface of the tip and a plurality of fluid channels, wherein the plurality of fluid channels terminate on a side surface of the tip;
- a receptacle, comprising a recessed region to removably couple the tip to the hand piece, wherein the receptacle comprises a first fluid channel opening that is coupled to a plurality of second fluid channel openings formed in the recessed region, and the first fluid channel opening is situated between the plurality of second fluid channel openings, and
- when the tip is coupled to the receptacle, the second fluid channel openings are coupled to a plurality of third fluid channel openings of the tip, and a back of the tip blocks flow of the first fluid channel opening and alters the flow from the first fluid channel opening to the second fluid channel openings;
- a vacuum opening, coupled to a vacuum tube coupled to the console, wherein the vacuum opening is outside a periphery of the tip; and
- a plurality of radiation sources, each radiation source coupled to an electrical wire coupled to the console, wherein the radiation sources are separate from the tip, and the tip is replaceable independently of the radiation sources.

2. The device of claim 1 wherein the plurality of radiation sources are between the tip and the vacuum opening.

3. The device of claim 1 wherein the plurality of radiation sources are evenly distributed about a perimeter of the front surface of the tip.

4. The device of claim 3 wherein the plurality of radiation sources irradiate a region of tissue between the perimeter of the front surface of the tip and the vacuum opening.

5. The device of claim 1 wherein an angle between the radiation sources is 360 degrees divided by a total number of radiation sources.

6. The device of claim 1 wherein the plurality of radiation sources are positioned within the receptacle of the hand piece or on a same plane as the tip, wherein the receptacle is farther from a skin surface than the tip.

7. The device of claim 1 wherein the plurality of radiation sources comprise at least one of a light emitting diode, a laser diode, a radio frequency diode, or a microwave antenna.

8. The device of claim 1 wherein at least one radiation source in the plurality of radiation sources emits a light beam having a wavelength that is in the visible range.

9. The device of claim 1 further comprising a radiation source holder, wherein the plurality of radiation sources are mounted to the radiation source holder and the radiation source holder is made of a thermally conductive plastic.

10. The device of claim 1 wherein the hand piece comprises:
a vibrating component;
a battery; and
a switch, coupled between the vibrating component and the battery.

11. The device of claim 10 wherein the vibrating component comprises:
a motor;
a weight; and
a shaft, coupled between the motor and the weight.

12. The device of claim 1 wherein when the tip is coupled to the receptacle, the plurality of second fluid channel openings of the recessed region mate with the plurality of third fluid channel openings of the tip to form complete fluid channel openings at the side surface of the tip.

13. The device of claim 1 wherein a cross section of a fluid channel of the plurality of fluid channels terminating on the side surface of the tip comprises a portion of the receptacle and a portion of the tip.

14. The device of claim 1 further comprising a temperature sensor coupled to the tip of the hand piece for measuring a temperature of the radiation sources or a tissue to be treated, wherein the temperature sensor is further coupled to a control unit of the console.

15. The device of claim 14 wherein the temperature sensor is electronically coupled to the control unit of the console.

16. The device of claim 14 wherein the temperature sensor sends a temperature value to the control unit,
when the temperature value is below a first threshold value, the control unit causes an increase of power to the radiation sources, and
when the temperature value is below a second threshold value, the control unit causes a decrease in power to the radiation sources.

17. The device of claim 1 wherein the plurality of radiation sources emit light in a first direction to a tissue, and the light does not pass through the tip.

18. A micro dermabrasion device comprising a hand piece comprising:
an elongated handle comprising a first passageway and a second passageway, wherein the first and second passageways extend from a proximal end to a distal end of the handle;
a tip holder, coupled to the distal end of the handle, comprising at least a first opening coupled to the first passageway and a plurality of second fluid channels, wherein the second fluid channels are coupled to the first opening, the second fluid channels extend radially from the first opening along a first conical curved surface of the tip holder, and the tip holder is adapted to removably couple to a tip comprising a second conical curved surface that mates with the first conical curved surface;
a second opening, coupled to the second passageway; and
a plurality of radiation sources, coupled to the handle, and a distance between a radiation source and an edge of the tip is less than twice a longest distance across a face of the tip, wherein the radiation sources are separate from the tip, and the tip is replaceable independently of the radiation sources.

19. The device of claim 18 wherein a cross section of the first and second passageways comprises concentric circles, an inner circle is for the first passageway, and an outer circle is for the second passageway.

20. The device of claim 19 wherein the first passageway provides output fluid and the second passageway provides suction.

21. The device of claim 19 wherein the first passageway provides suction and the second passageway provides output fluid.

22. The device of claim 19 wherein the tip comprises an abrasive surface, and at least one of the radiation sources is outside a periphery of the abrasive surface of the tip.

23. The device of claim 18 wherein at least one of the radiation sources is positioned between the first opening and the second opening.

24. The device of claim 18 wherein a cross section of the tip holder comprises at least two concentric spaces, a first space of the concentric spaces is coupled to the first opening, and a second space of the concentric spaces is coupled to the second opening.

25. The device of claim 18 comprising:
a lens, coupled to a housing of at least one radiation source, covering the at least one radiation source and providing magnification of radiation emitted by the at least one radiation source.

26. The device of claim 18 comprising:
a housing for at least one radiation source, the housing comprising a locking mechanism to removably hold a lens over the at least one radiation source.

27. The device of claim 18 wherein the tip holder comprises a first surface formed on a front surface of the tip holder, wherein the first surface contacts skin to be treated, and the plurality of radiation sources are positioned on a same plane as the first surface of the tip holder.

28. The device of claim 18 wherein a cross section of the first and second passageways comprises concentric rings, an inner ring is for the first passageway, and an outer ring is for the second passageway.

29. The device of claim 28 further comprising a radiation source holder, wherein the plurality of radiation sources are mounted to the radiation source holder, and the radiation source holder is positioned between the inner and outer rings.

30. The device of claim 29 wherein the first passageway provides an output fluid and the second passageway provides suction, the output fluid flows over the radiation source holder in a first direction from the first passageway to the second passageway, and at least one of the plurality of radiation sources emits a first light in a second direction, wherein the first direction intersects with the second direction at an angle.

* * * * *